United States Patent
Hayasaki et al.

(10) Patent No.: US 6,423,977 B1
(45) Date of Patent: *Jul. 23, 2002

(54) PATTERN SIZE EVALUATION APPARATUS

(75) Inventors: Kei Hayasaki; Shinichi Ito; Kenji Kawano; Soichi Inoue; Katsuya Okumura, all of Yokohama (JP)

(73) Assignee: Kabushiki Kaisha Toshiba, Kawasaki (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/030,510

(22) Filed: Feb. 25, 1998

(30) Foreign Application Priority Data

Feb. 26, 1997 (JP) ............................................. 9-042245
Feb. 23, 1998 (JP) ........................................... 10-040603

(51) Int. Cl.$^7$ ............................................. G01N 21/86
(52) U.S. Cl. ............................. 250/559.19; 250/559.44; 356/237.5
(58) Field of Search ................... 250/559.19, 559.44, 250/550, 559.2, 559.24, 559.26, 559.27, 559.22; 356/354, 384, 355, 394, 237.4, 237.5; 430/30, 311

(56) References Cited

U.S. PATENT DOCUMENTS

| | | | | |
|---|---|---|---|---|
| 4,142,107 A | * | 2/1979 | Hatzakis et al. | 250/559.22 |
| 4,303,341 A | * | 12/1981 | Kleinknecht et al. | 356/384 |
| 4,408,884 A | * | 10/1983 | Kleinknecht et al. | 356/355 |
| 4,815,854 A | * | 3/1989 | Tanaka et al. | 356/356 |
| 4,953,982 A | * | 9/1990 | Ebbing et al. | 356/357 |
| 5,076,692 A | * | 12/1991 | Neukermans et al. | 356/338 |
| 5,164,790 A | * | 11/1992 | McNeil et al. | 356/355 |
| 5,361,137 A | * | 11/1994 | Aton et al. | 356/354 |
| 5,422,723 A | * | 6/1995 | Paranjpe et al. | 356/355 |
| 5,777,729 A | * | 7/1998 | Aiyer et al. | 356/237.1 |

OTHER PUBLICATIONS

K. Suwa et al., "Automatic laser scanning focus detection method using printed focus pattern", SPIE, vol. 2440, pp. 712–720, Feb. 1995.
H.P. Kleinknecht et al., "Linewidth measurement on IC masks and wafers by grating test patterns", Applied Optics, vol. 19, No. 4, pp. 525–533, Feb. 15, 1980.
J.R. McNeil et al., "Scatterometry applied to microelectronics processing—Part 1", Solid State Technology, pp. 29–32, Mar. 1993.

* cited by examiner

Primary Examiner—Que T. Le
Assistant Examiner—Thanh X. Luu
(74) Attorney, Agent, or Firm—Finnegan, Henderson, Farabow, Garrett & Dunner, L.L.P.

(57) ABSTRACT

A pattern size evaluation apparatus comprising an illumination optical system for projecting parallel light rays of a predetermined wavelength on a monitoring area formed on an object, the monitoring area being formed at a position different from a device pattern formed on the object, a light intensity detection optical system for detecting diffracted light from the monitoring area, and a device pattern size evaluation section for evaluating a size of the device pattern based on an intensity of diffracted light from the monitoring area.

13 Claims, 15 Drawing Sheets

MOVING METHOD FOR
HEAD TO MONITORING AREA

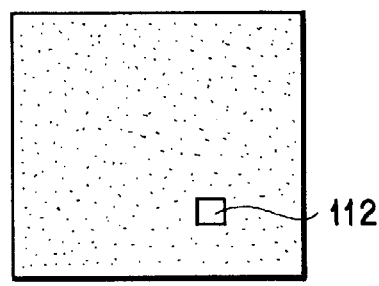
F I G. 16A
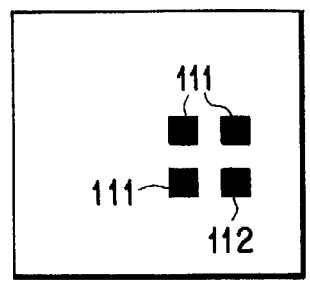
F I G. 16B
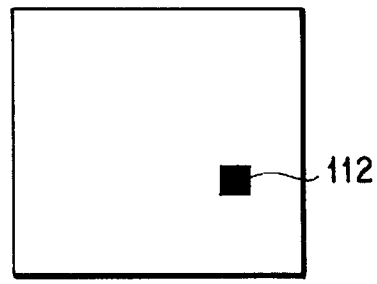
F I G. 16C
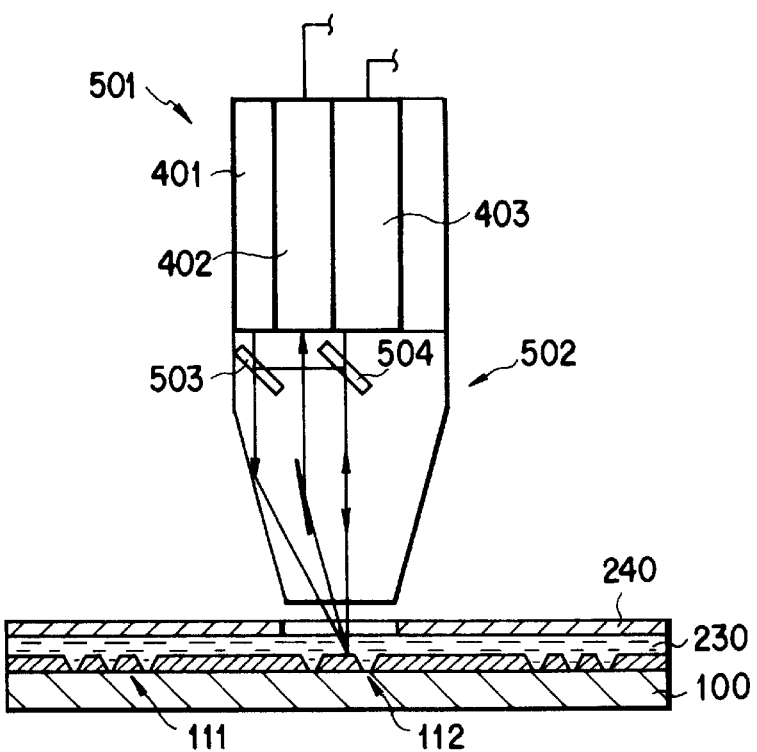
F I G. 17

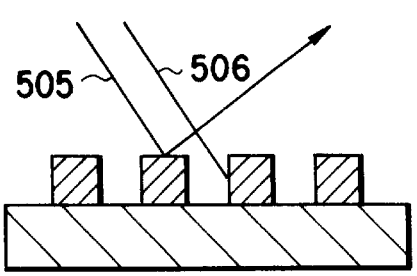
F I G. 18A
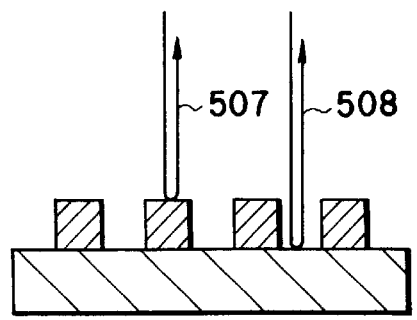
F I G. 18B
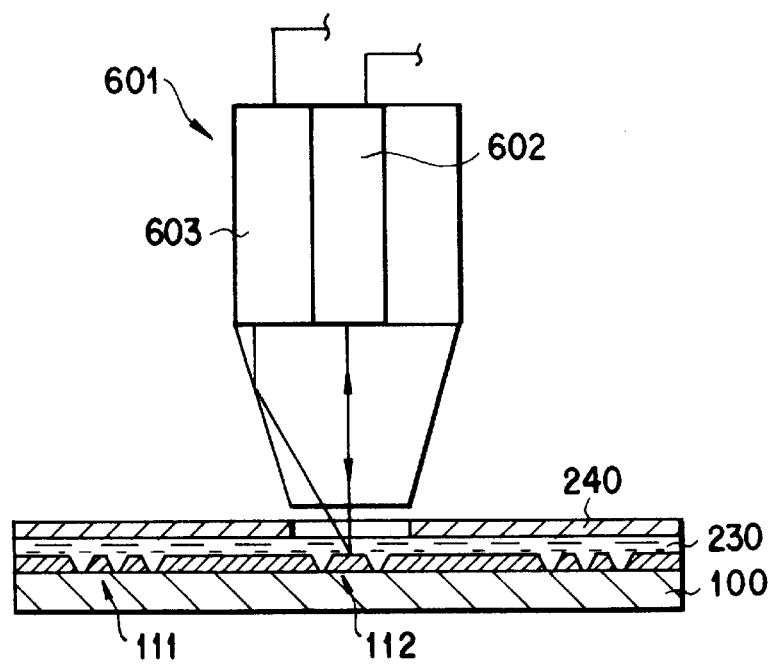
F I G. 19
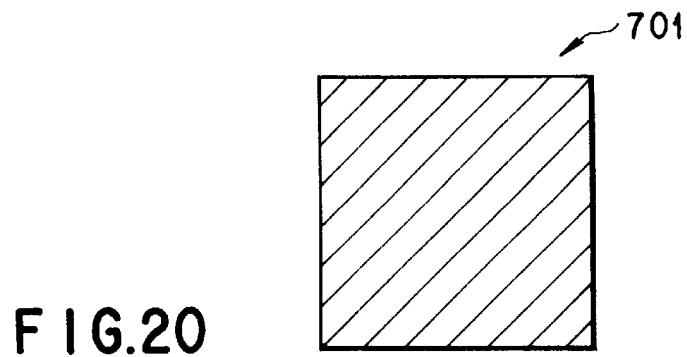
F I G. 20

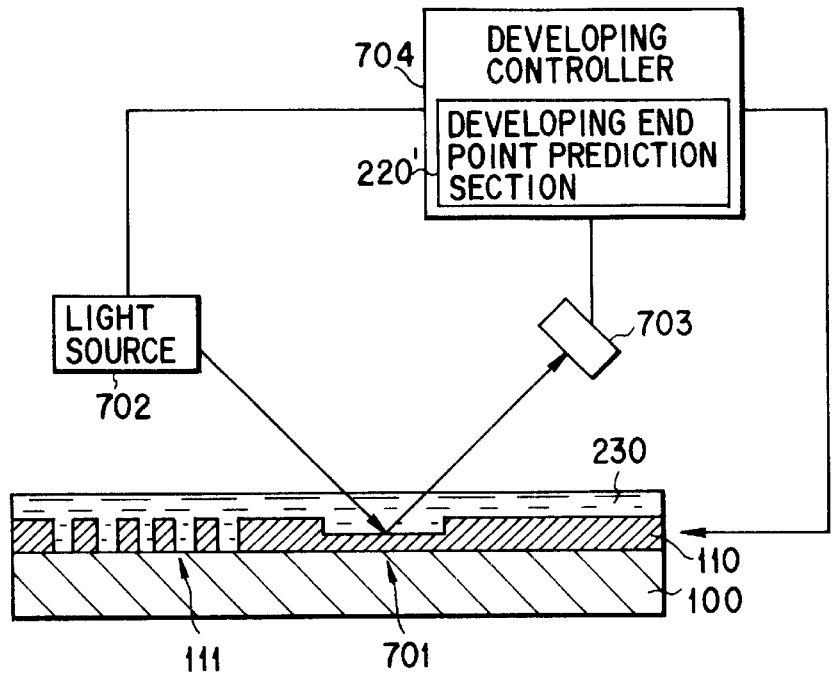
F I G. 21
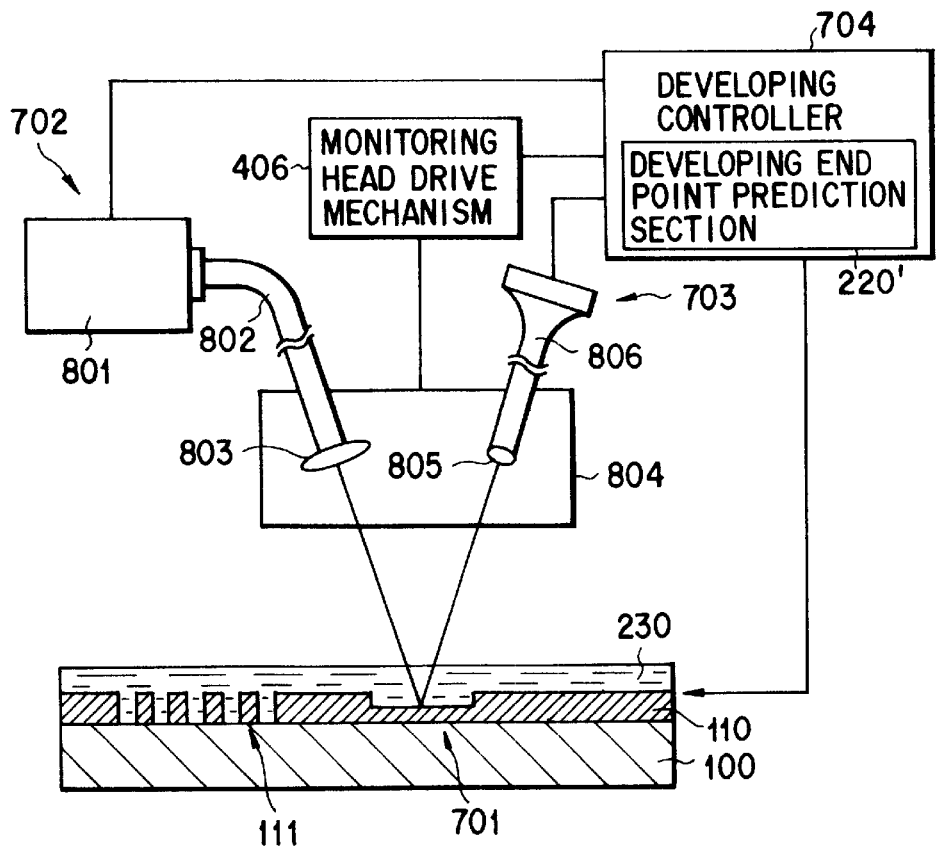
F I G. 23

PATTERN SIZE EVALUATION APPARATUS

BACKGROUND OF THE INVENTION

The present invention relates to an optical lithographic technique of forming a resist pattern in semiconductor device fabrication and more particularly, a pattern size evaluation apparatus for evaluating a resist pattern during or after developing.

In order to form an integrated circuit pattern on a wafer, a desired pattern is projected on resist on exposure after resist is applied on the wafer, the resist is developed to a resist pattern and the resist pattern is used as a mask to perform processing such as etching or the like. A resist pattern as a mask is required a high size accuracy and a size of the resist pattern is changed in dependence on elapsed time in developing to an great extent. Therefore, control of a developing time is very important.

Conventionally, size control in developing has been performed with a constant developing time. That is, at first, a preceding wafer is exposed to light and developed in order to determine an optimum developing time. Then, all the other wafers are developed with the optimum developing time as a constant time.

However, in actual cases, a history of each wafer in process, such as a post exposure delay and the like, is different from another. Therefore, if wafers of the same lot are subjected to developing in the same time, a dispersion in size between the wafers arises, so that developing cannot be terminated with a desired size for every wafer.

Though such control for developing time has so far been adopted, there has arisen no severe problem since an error in size is within an allowable range.

However, nowadays, miniaturization in the process is progressed and more accurate size control has been required, which makes size control in developing harder, if with the conventional means, for controlling a developing time.

On the other hand, evaluation of a resist pattern after developing has conventionally performed by, for example, SEM (Scanning Electron Microscope). While SEM enables pattern observation under high magnification, it is complex in apparatus structure and expensive. Moreover, since it takes a very long time for inspection, it is harder to be efficient in evaluation.

In the cases where a device pattern is optically inspected by use of diffracted light and the like during developing or after developing, information from an inspected pattern sometimes includes information from another pattern in monitoring, which has been a factor to make accuracy in monitoring deteriorated.

BRIEF SUMMARY OF THE INVENTION

The present invention has been made in consideration of the above mentioned circumstances and it is an object of the present invention to provide a pattern size evaluation apparatus, which makes it possible to perform size control of a resist pattern on a different wafer with high accuracy.

It is another object to provide an pattern size evaluation apparatus which makes it possible to inspect a resist pattern in a short time with high accuracy without reception of an influence of a pattern other than a pattern to be monitored.

It is a further object to provide an pattern size evaluation apparatus which makes it possible to evaluate a resist pattern during developing in a short time with high accuracy and to predict an end point of developing with high accuracy.

In order to solve the above problems, a pattern size evaluation apparatus comprising: an illumination optical system for projecting parallel light rays of a predetermined wavelength on a monitoring area formed at a position different from a device pattern on an object; a light intensity detection optical system for detecting diffracted light from the monitoring area; and a device pattern size evaluation section for evaluating a size of the device pattern based on an intensity of diffracted light from the monitoring area.

The apparatus can be applied for evaluation of a device pattern size after developing is terminated or applied for detection of an end point of developing of the device pattern. Where the apparatus is applied to detect an end point of developing of a device pattern, the apparatus comprises a section for judging the end point of developing based on a change in intensity of diffracted light from the monitoring area.

As the monitoring area, in the first place, a monitoring area, which comprises a monitoring pattern, is preferred. The monitoring pattern comprises an element pattern different from a device pattern so that diffracted light from the monitoring pattern is detected by being separated from diffracted light of the device pattern. The monitoring pattern is preferably a pattern, through which resist is exposed, and which comprises elements thereof are in a proximity relation periodically disposed so that a distance between adjacent pairs of the elements is equal to or less than the limit of resolution.

In this case, it is only required that pattern size evaluation section performs pattern evaluation based on a relation obtained in advance between the size of a device pattern and the intensity of diffracted light from the monitoring pattern.

In the second place, the monitoring area may be formed by exposing such that the monitoring area will be etched at a uniform developing speed across the whole area and decrease in fi thickness gradually.

In this case, the monitoring area is formed by being exposed in the same condition as that of the device pattern. That is, the mask pattern for forming the monitoring area is formed on the same plane as a mask patter for device pattern is formed. The mask pattern for forming the monitoring area may be a pattern with a pitch thereof which reaches the object only with diffracted light of order 0 in the exposure condition. Then a ratio in area between transmission area and block area in the mask pattern for forming the monitoring area is designed so that decrease in film thickness arises gradually in a uniform manner in company with progress of developing.

In this case, as illumination light projected on the monitoring area from illumination system, it is preferred that the light have a wavelength with which a change in intensity of diffracted light has maximums and minimums in the course of decrease in film thickness of the monitoring area. And the section for predicting an end point of the developing predicts the end point of developing based on detected maximums and minimums of diffracted light intensity, or detected maximum and minimum of a value of the derivative of a change in diffracted light intensity with respect to time.

Further, as a monitoring area, in the third place, the area may be a monitoring region in which exposure is performed so that a film thickness is to be a predetermined value with a timing determined based on an end point of developing for a device pattern. In this case, it is only required that means for predicting an end point of developing is to determined the end point of developing by detecting the timing when the film thickness becomes the predetermined value.

According to the present invention, a size inspection of device pattern is performed with use of a monitoring area comprising an element which is discernible from a device pattern and an already processed pattern.

In the case where a monitoring pattern is formed in a monitoring area by exposure, for example, a circle or a polygon is used as an element pattern of an exposure mask for forming the monitoring pattern, and a distance between adjacent element patterns is designed so as to be equal to or less than the limit of resolution in exposure to light. With a monitoring pattern formed in such a manner, a change thereof in intensity of diffracted light is larger than that from a device pattern and thereby accuracy in inspection can be improved.

If a pitch, a monitoring pattern of a direction of repetition thereof or the like being different, is used for evaluation of a pattern, a inspection with high accuracy, which is not affected by another pattern, can be performed. Moreover, since a pattern evaluation can be performed only by monitoring an intensity of diffracted light, an inspection can be conducted in a short time, which is different from SEM and the like.

In the case where as a monitoring area, a monitoring area is used which has no pattern as mentioned above, which is exposed so that a almost uniform developing speed is achieved across the whole surface, and with which an almost uniform decrease in film thickness is achieved as developing progresses, maximums and minimums of an intensity of diffracted light from the monitoring area can be observed. An end point of developing can be predicted based on the maximums and minimums.

According to such a prediction method, even when an offset in terms of a sign to be attached to an absolute value of an intensity signal of diffracted light arises, a correct end point of developing can be obtained by correcting the offset, since it is so arranged that an end point in developing is predicted based on maximums or minimums.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIGS. 16A, 16B and 16C are views showing an example of detection of a monitoring pattern in the sixth embodiment;

FIG. 17 is a view showing an example of a construction of an apparatus for performing pattern inspection during developing with use of diffracted light of order 0, which is a view for illustrating a seventh embodiment;

FIGS. 18A and 18B are views for illustrating optical paths of diffracted light of order 0 in the seventh embodiment;

FIG. 19 is a view showing an example of a construction of an apparatus for performing pattern inspection during developing with use of diffracted light of order 0, which is a view for illustrating a eighth embodiment;

FIG. 20 is a schematic view showing a monitoring area used in a ninth embodiment, which is the view for illustrating the ninth embodiment;

FIG. 21 is a view showing an example of a construction of an apparatus for performing pattern inspection during developing with use of diffracted light of order 0, which is a view for illustrating the ninth embodiment;

FIG. 23 is a view showing an example of a construction of an apparatus for performing pattern inspection during developing with use of diffracted light of order 0, which is a view for illustrating a tenth embodiment;

DETAILED DESCRIPTION OF THE INVENTION

Figure 1:
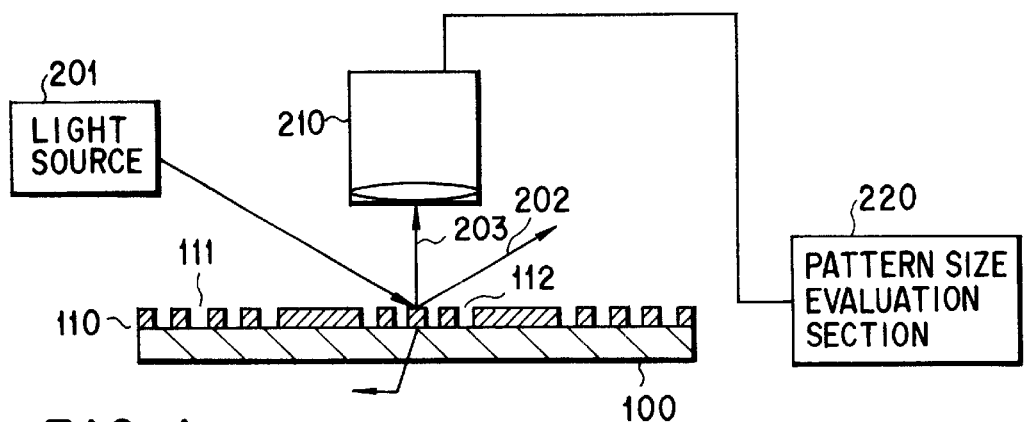
FIG. 1 is a view showing an example of a construction of an apparatus for performing pattern inspection after developing with use of a diffracted light of order 1, which is a view for illustrating a first embodiment.

Details of the present invention will below be described in reference to embodiments shown in the drawings.

(The First Embodiment)

FIG. 1 is a view for illustrating an apparatus for performing pattern inspection according to the first embodiment of the present invention. FIG. 1 shows an example of a construction of the apparatus in which a pattern inspection after developing with use of a diffracted light of order 1.

A device pattern 111 is formed by full-wafer exposure and a developing treatment together with a monitoring pattern 112 in resist 110 on a wafer (object to be treated) 100. The monitoring pattern 112 is disposed in a spaced manner from an area contributing to device formation within one shot.

Parallel light rays having a wavelength in the range of 400±20 nm are projected through a narrow band filter from a light source 201 to the monitoring pattern 112. Diffracted light of orders 0 and 1 (202, 203) and larger numbers (not shown) are obtained from the monitoring pattern 112. The diffracted light of order 0 (202) from the monitoring pattern 112 is detected by a CCD camera 210. The CCD camera 210 is connected to a pattern evaluation section 220 comprising a computer system. The pattern evaluation section 220 performs evaluation of a device pattern size by applying to a pre-detected relation between the size of the pattern and the intensity of diffracted light of order 1.

Figure 2:
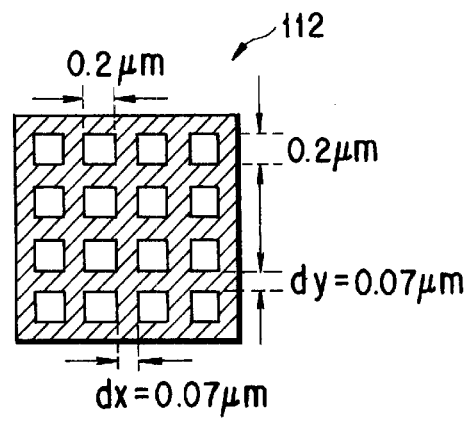
FIG. 2 is a view showing an example of a monitoring pattern in the first embodiment.

FIG. 2 is a view showing an example of a developing monitoring pattern 112 in the present embodiment. Plural squares of a side L=0.2 µm (wafer conversion value, hereinafter expressed in the same way) are regularly disposed in such a manner that centers of 4 squares disposed adjacent to one another respectively occupy respective vertexes of a quadrangle. A distance along an x direction dx and a distance along y direction dy between adjacent squares are both 0.07 µm. Values of the distances dx, dy=0.07 µm are those equal to or less than the limit of resolution of an exposure equipment.

An L & S pattern of 0.15 µm was considered as the device pattern 111. Exposure conditions were that a wavelength of exposure light=248 nm (KrF excimer laser), a numerical number (NA) of a projection optical system=0.7, a coherence factor (σ)=0.75 and an illumination is a ⅔ zone plate illumination, and as a resist, a positive chemical amplification resist with a thickness of 0.15 µm is used.

Exposure was conducted with a monitoring pattern 112 of the following sizes in such conditions as an L & S device pattern of 0.15 µm (line width : space width=1:1) 111 is completed to a desired size in a developing time of 30 sec:

(a) . . . the monitoring pattern shown FIG. 2.

(b) . . . an L & S monitoring pattern of 0.15 µm (line width: space width=1:1)

(c) an L & S monitoring pattern of 0.15 µm (finish line width: space width=1:3)

(d) . . . an L & S monitoring pattern of a line width of 0.07 µm and a space width of 0.2 µm, where since (b) is the same size as that of the device pattern 111, relation between a change in intensity of diffracted light of order 1 and a change in size of the device pattern 111 can be known by comparison with (b).

Figure 3:
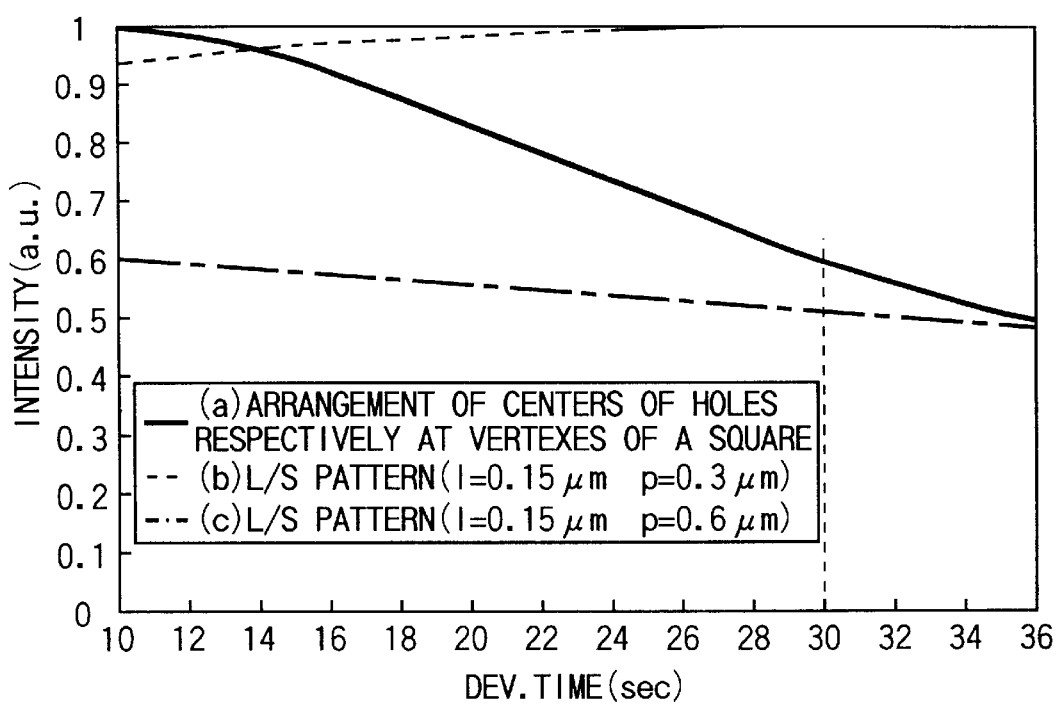
FIG. 3 is a graph showing a relation between the developing time and the intensity of the diffracted light of order 1 in the first embodiment.

A relation between developing times (10 to 36 sec) and intensities of diffracted light of order 1 for (a) to (d) after developing is over is shown in FIG. 3. At this time, since a pattern of (d) was not developed at all, no data are shown in the graph.

At a time point near an end of developing, the pattern (b) showed almost no change in the intensity and the pattern (a) showed a change in the intensity larger than the case of the pattern (c) by a factor of about 4. In this case, a change in the intensity of the pattern (a) was 10 for a change of 1.5 nm in a size of the L & S pattern of 0.15 µm(b) where a gradation of a CCD camera is 256.

As a cause for this result, the following is estimated:

When a repetition pitch of patterns is indicated by p, and a distance between lines, a reflectance, a phase in a line portion are respectively indicated by 1, $r_a$, $\phi_a$, and a reflectance and a phase in a space portion are indicated by $r_b$, $\phi_b$, an intensity of light of order m is expressed in the following formula as shown in H. P. Kleinknecht and H. Meier, Applied Optics, Vol. 19, No. 4 (1980) pp. 525 to 533.

$$I(m) \propto \frac{\sin^2(m\pi 1/p)}{m^2 \pi^2}\{|r_a|^2 + |r_b|^2 - 2|r_a||r_b|\cos(\phi_a - \phi_b)\}$$

Figure 4:
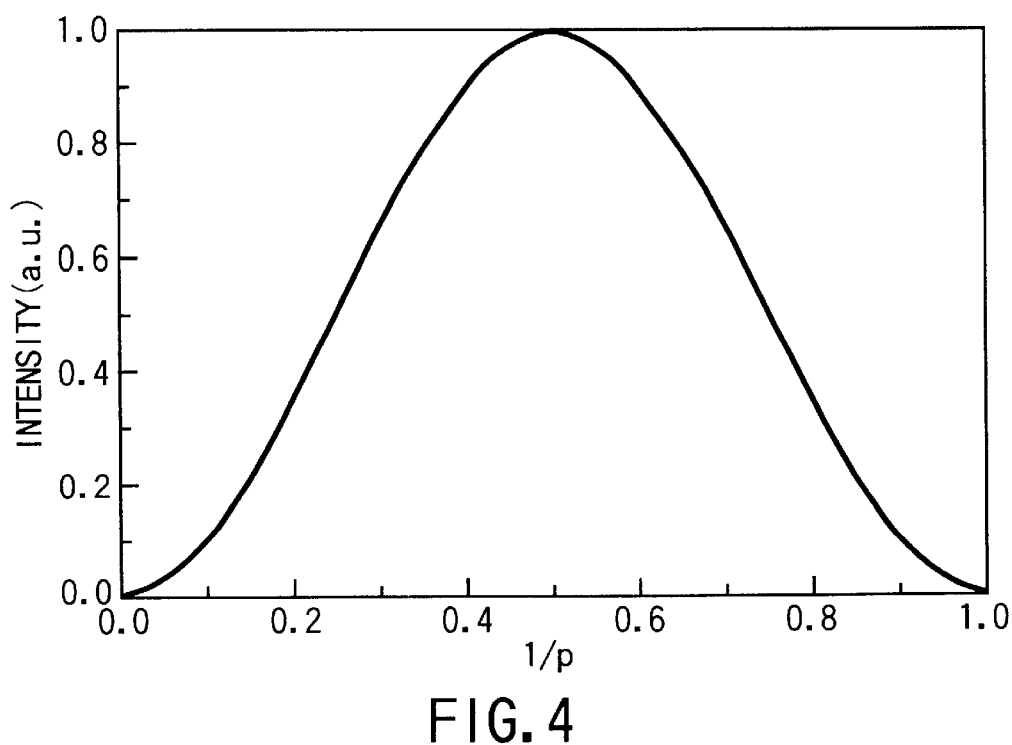
FIG. 4 is a graph showing a relation between the ideal ratio of a pitch and a line width and the intensity of diffracted light of order 1.

According to a relation in the formula, it is required that a change in a line width occurs in the vicinity of 1/p=0.25 or 0.75 in order to obtain a larger change in the intensity (see FIG. 4).

It is considered that the reason why is that since a change in a line width of the monitoring pattern (a) occurs in the vicinity of 1/p=0.25, a change in the intensity is the maximum. Since the L & S pattern (d) which has the same pitch as the pattern (a) but a different space width from the pattern (a) showed no change in the intensity, being a pattern in the shape of a hole is important.

As described above, according to the present embodiment, if a monitoring pattern of a size is larger as compared with a device pattern 111 in a change in intensity of diffracted light of order 1 is used, a change in a size of 1.5 nm can be measured by 10 gradation units of a CCD camera having a 256 gradation.

That is, in the L & S pattern (b) of 0.15 µm (a line width: a space width=1:1) which is the same size of the device pattern 111, a degradation changes only one unit for a change of 5% in size (7.5 nm). On the other hand, if a monitoring pattern (a) of a pattern width of which is equal to or less than the limit of resolution of an exposure equipment is monitored, measurement accuracy can be greatly improved, since a smaller change in size can be detected with a larger number of gradation units.

Further, since pattern evaluation is performed by optical means, pattern evaluation of a wafer is easier to be performed and thereby a throughput is improved. Moreover if a CCD camera with a 1024 gradation is used in monitoring, accuracy can simply be increased by a factor of 4.

(The Second Embodiment)

Figure 5:
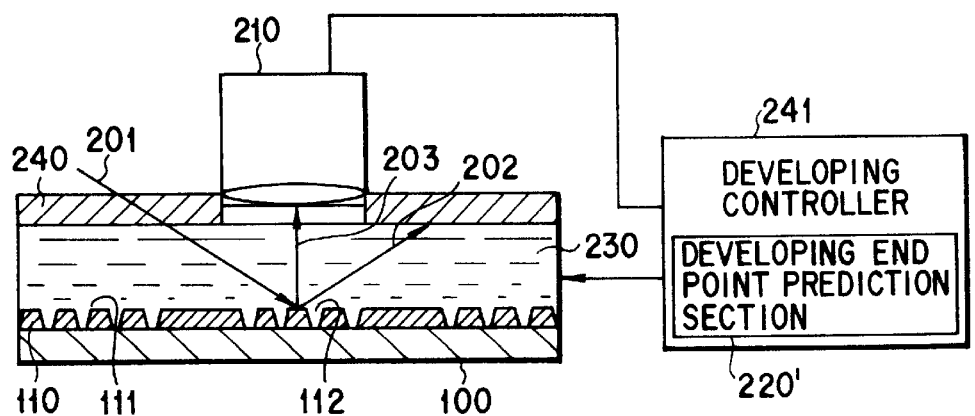
FIG. 5 is a view showing an example of a construction of an apparatus for performing pattern inspection during developing with use of diffracted light of order 1, which is a view for illustrating a second embodiment.

FIG. 5 is a view showing an example of a construction of an apparatus for performing pattern inspection during developing with use of diffracted light of order 1, which is a view for illustrating a second embodiment. That is, FIG. 5 shows an example of an in-situ developing monitor using diffracted light of order 1.

While a fundamental construction of the monitor is the same of FIG. 1, a developer 230 is present on a resist 110 and a nozzle in the shape of a disc is placed thereon. The CCD camera 210 is connected to a developing controller 241 which controls process conditions, such as a developing time and the like. The developing controller 241 comprises a developing end point prediction section 220' which predicts an end point in developing of the device pattern 111 based on an intensity of diffracted light from the monitoring pattern 112.

In this apparatus, parallel light rays 201 having a wavelength of 400 nm +20 nm which does not optically activate resist is projected to the monitoring patter 112 during developing through a narrow band filter in a direction oblique to the monitoring pattern 112. While the monitoring pattern 112 is disposed in a spaced manner from an area contributing to device formation within one shot, the device pattern 111 and the monitoring pattern 112 are differently designed in pitch.

Figure 6:
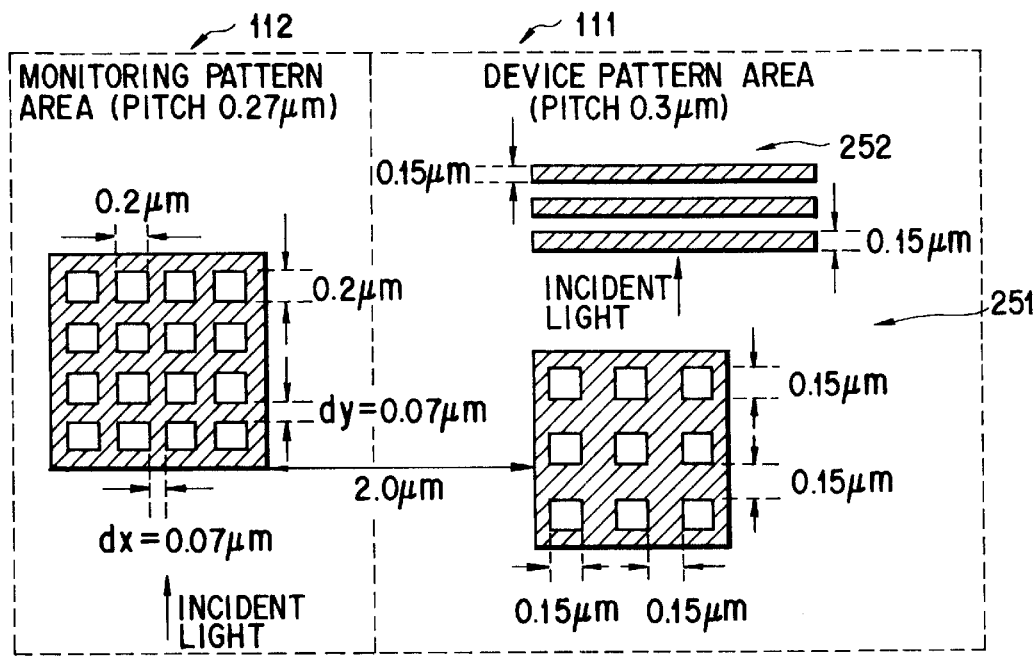
FIG. 6 is a view showing an example of a device pattern and a monitoring pattern in the second embodiment.

In a concrete manner, as shown in FIG. 6, the device pattern 111 comprises a L & S pattern 251 of 0.15 $\mu$m or a hole pattern 252 of a pitch of 0.30 $\mu$m in a very close area. An already processed layer is present in an lower layer, and in the already processed layer, there is a L & S device-pattern of 0.15 $\mu$m or a hole device-pattern of a pitch of 0.3 $\mu$m.

As a monitoring pattern, the same pattern as that shown in FIG. 2 is used. That is, in the monitoring pattern 112, plural squares of a side L=0.2 $\mu$m are regularly disposed and a distance along an x direction dx and a distance along y direction dy in adjacent squares are both 0.07 $\mu$m. Values of the distances dx, dy=0.07 $\mu$m are those equal to or less than the limit of resolution of an exposure equipment.

Diffracted light of order 1, 203 from the developing monitoring pattern 112 is detected by a CCD camera 210. The developing end point prediction section 220' compares detected diffracted light of order 1 with a relation obtained in advance between the developing time and the intensity of diffracted light of order 1. The section 220' sets a time when an intensity of diffracted light assumes a desired value as an end point of the developing. The developing controller 241 terminates the developing based on the detection.

In the present embodiment, since the device pattern 111 and the monitoring pattern 112 have different pattern pitches, it is possible to discern one from the other.

Figure 7:
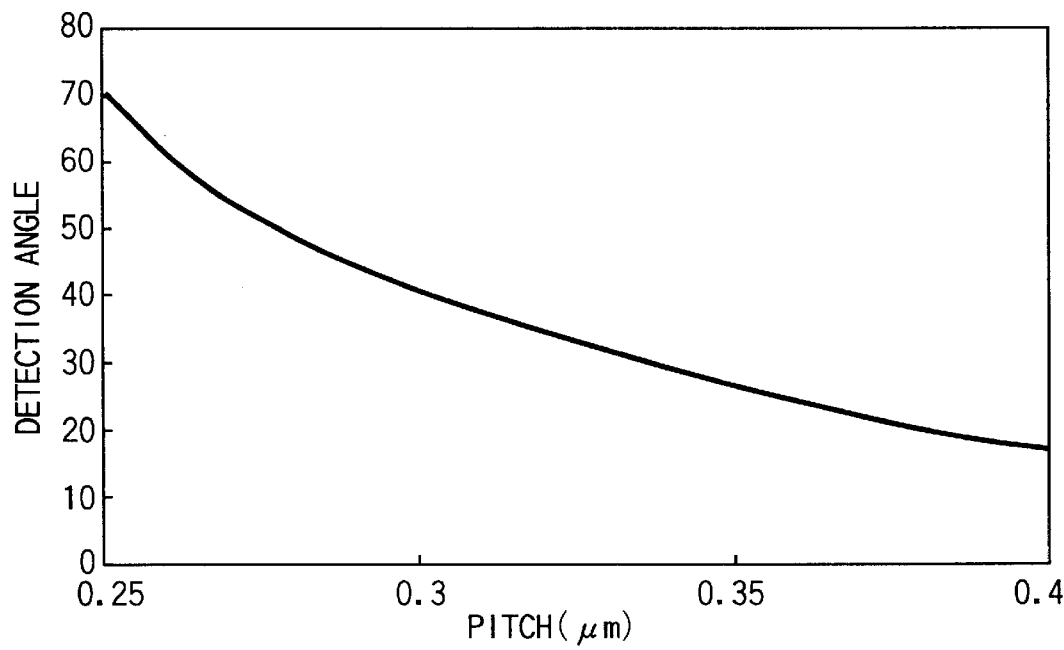
FIG. 7 is a graph showing a relation between the pitch of repetition and the detection angle.

When an incident angle is 40 degrees in FIG. 5, a relation between the detection angle and the pitch is shown in FIG. 7. As can be seen from the graph, when a pitch is 0.27 $\mu$m, a detection angle is 57 degrees and when a pitch is 0.30 $\mu$m, a detection angle is 44 degrees. Therefore, even when the device pattern 111 and the monitoring pattern 112 are disposed in very close areas to each other, diffracted light of order 1 from the device pattern 111 and the already processed pattern are discernible from diffracted light of order 1 from the monitoring pattern 112 if respective pattern pitches are different.

As described above, according to the present embodiment, if the monitoring pattern 112 whose pitch is different from the device pattern 111 or the already processed pattern is used, good monitoring can be performed with excellent accuracy without receiving any influence of diffracted light other than the monitoring pattern 112. For this reason, an end point of developing can correctly judged and thus accurate control in size of a resist pattern can be achieved.

(The Third Embodiment)

While the present embodiment has a similar construction to that of the second embodiment (FIG. 5), a position of a monitoring pattern 112 is different.

In the apparatus, parallel light rays 201 of a wavelength of 390±10 nm which does not optically activate resist is projected to a monitoring pattern 112 during developing through a narrow band filter in a direction oblique to the monitoring pattern 112. While the monitoring pattern 112 is disposed at a position spaced apart from an area which contribute to formation of a device within one shot, the device pattern 111 and the monitoring pattern 112 are designed so as to be different from each other in a direction of repetition.

Figure 8:
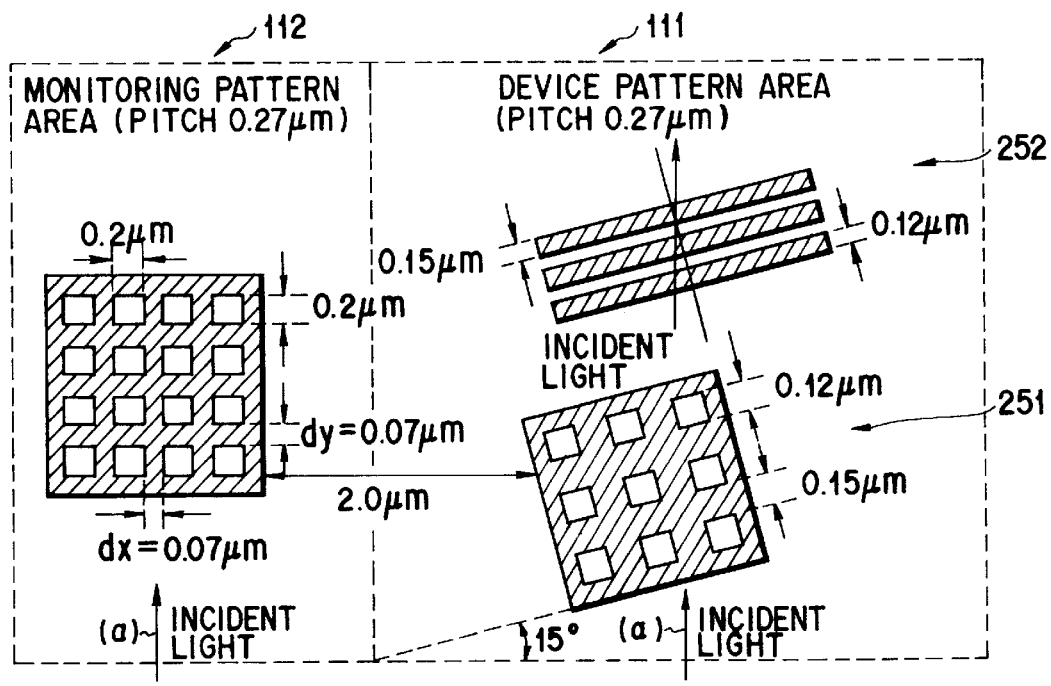
FIG. 8 is a view showing an example of a device pattern and a monitoring pattern in a third embodiment.

In a concrete manner, as shown in FIG. 8, the device pattern 111 comprises an L & S pattern 252 of a pitch of 0.27 $\mu$m and a hole pattern 251 of a pitch of 0.27 $\mu$m being respectively disposed in areas very close to each other. These device patterns 251, 252 are formed and disposed so that their directions of repetition are different by 15 degrees from that of the monitoring pattern 111.

In such a situation, diffracted light of order 1 (203) from the developing monitoring pattern 112 is detected by a CCD camera 210. A derivative of detected intensity of the diffracted light of order 1 with respect to time is compared with a relation obtained in advance between the developing time and the intensity of diffracted light of order 1. Then, a time when a derivative of an intensity of diffracted light of order 1 assumes a desired value is set as an end point in the developing.

If light is projected at an angel of 30 degrees to a pattern surface in a direction shown as an arrow ($\alpha$) in FIG. 8, while diffracted light of order 1 from the monitoring pattern 112 is detected in the same direction as the incident light and normal to the pattern surface, diffracted light of order 1 from the device pattern 111 is detected in a direction different from the incident light. Therefore, when directions of repetition are different, diffracted light can be separated even though pitches are the same.

As described above, according to the present embodiment, if the monitoring pattern 112 of the repetition direction is different from the device pattern 111 or already processed pattern is used, good monitoring can be performed with excellent accuracy without receiving any influence of diffracted light other than the monitoring pattern 112. For this reason, an end point in developing can correctly judged same as the second embodiment and thus accurate control in size of a resist pattern can be achieved.

(The Fourth Embodiment)

While the present embodiment has a similar construction to that of the second embodiment (FIG. 5), a position of a monitoring pattern 112 is different.

In this apparatus, too, parallel light rays 201 of a wavelength of 390±10 nm which does not optically activate resist is projected to a monitoring pattern 112 during developing through a narrow band filter in a direction oblique to the monitoring pattern 112. An already processed monitoring pattern 112' of a pitch of 0.3 μm is present in an lower layer than the monitoring pattern 112.

As the developing monitoring pattern 112, a pattern of the same size as that shown in FIG. 2 is used. Widths dx, dy=0.07 μm are both values equal to or less than the limit of resolution.

Diffracted light 203 of order 1 from the monitoring pattern 112 in developing is detected by a CCD camera 210. A time difference, between the time when the derivative of detected intensity of the diffracted light of order 1 is detected and a time when the development is over, is calculated based on a relation obtained in advance between the developing time and the intensity of diffracted light of order 1. Then, an end point of the development is detected based on the time difference.

Where an incident angle of an incident light in FIG. 5 is 40 degrees, a relation between the detection angle and the pitch is expressed as shown in FIG. 7 described above. Since when a pitch is 0.27 μm, a detection angle is 57 degrees and when a pitch is 0.30 μm, a detection angle is 44 degrees. Therefore, if a different monitoring pattern is used for a different layer, diffracted light of order 1 from a monitoring pattern 112' in a lower layer can be separated from that from the monitoring pattern 112 in process.

According to the present embodiment, since a monitoring pattern different in pitch is used in a different layer, good monitoring can be achieved without receiving any influence of diffracted light of order 1 from a monitoring pattern in a lower layer, thus accurate control in size of a resist pattern can be achieved as in the second embodiment.

(The Fifth Embodiment)

Figure 10:
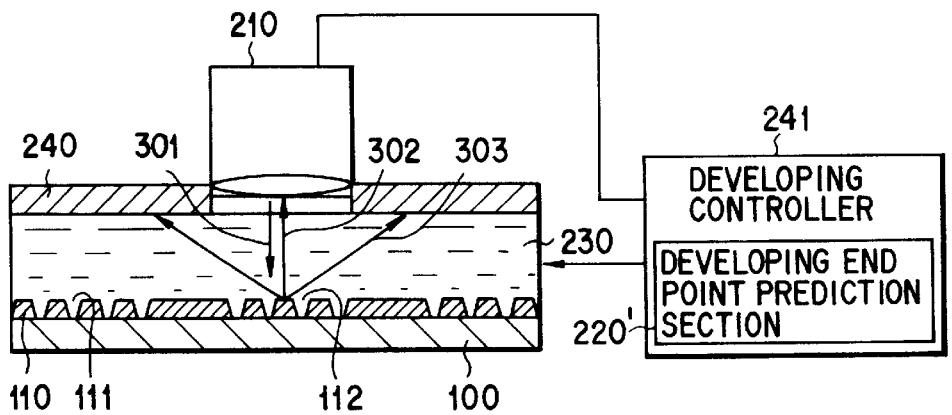
FIG. 10 is a view showing an example of a construction of an apparatus for performing pattern inspection during developing with use of the diffracted light of order 0, which is a view for illustrating a fifth embodiment.

FIG. 10 is a view showing an example of a construction of an apparatus for performing pattern inspection during developing with use of diffracted light of order 0, which is a view for illustrating a fifth embodiment. That is, FIG. 10 shows an example of an in-situ developing monitoring using diffracted light of order 0.

In the apparatus, collimated laser light 301 of a wavelength of 488 nm is projected to the monitoring pattern 112 during developing in a direction normal to the pattern. Only diffracted light 302 of order 0 of diffracted light from the monitoring pattern 112 in developing (diffracted light of order zero 302, diffracted light of order one 303 and the like) is detected by a CCD camera 210. A developing controller 240 (a developing end point prediction section 220') calculates an intensity of the diffracted light of order 0 by processing with a computer a pixel brightness of the CCD camera 210 and thus predicts an end point in developing of the device pattern 111 based on the calculated value.

Figure 11:
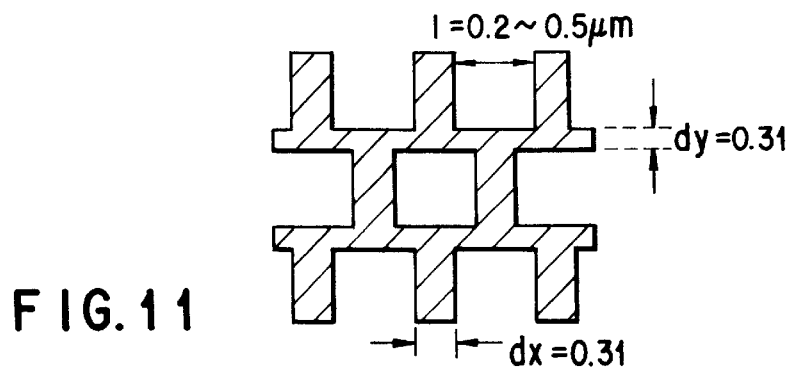
FIG. 11 is a view showing an example of a monitoring pattern in the fifth embodiment.

FIG. 11 is a view showing a developing monitoring pattern 112 as an image on a exposure mask in the present embodiment. Plural squares each of a side of L=0.2 μm are regularly disposed and vertexes of a triangle, which is solid by being packed with the plural squares, respectively assume the centers of squares. Widths of dx in a x direction and dy in a y direction are both 0.06 μm and the values are equal to or less than the limit of resolution. Since the squares are transferred on an actual wafer as a circular hole, the monitoring pattern 112 is a pattern in which plural holes are densely packed.

An L & S pattern of 0.15 μm was considered as the device pattern 111. Exposure conditions were under ⅔ annular illumination that a wavelength of exposure light=248 nm (KrF excimer laser), a numerical aperture (NA)=0.7 and a coherence factor (σ)=0.75 and positive chemical amplification resist of a film thickness of 0.15 μm was used.

Figure 12:
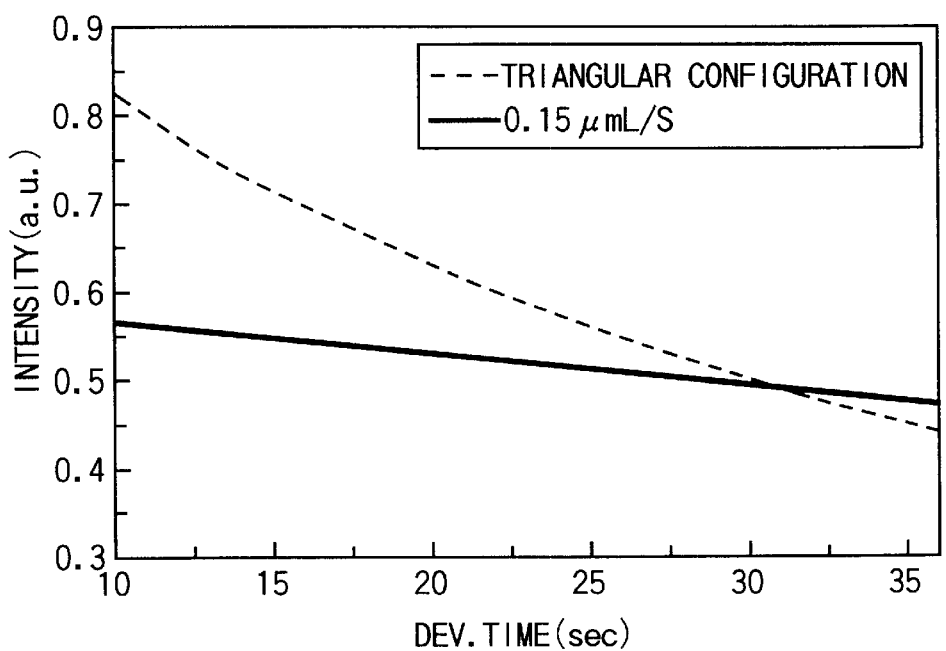
FIG. 12 is a graph showing a relation between the developing time and the intensity of the diffracted light of order 0 in the fifth embodiment.
Figure 9:
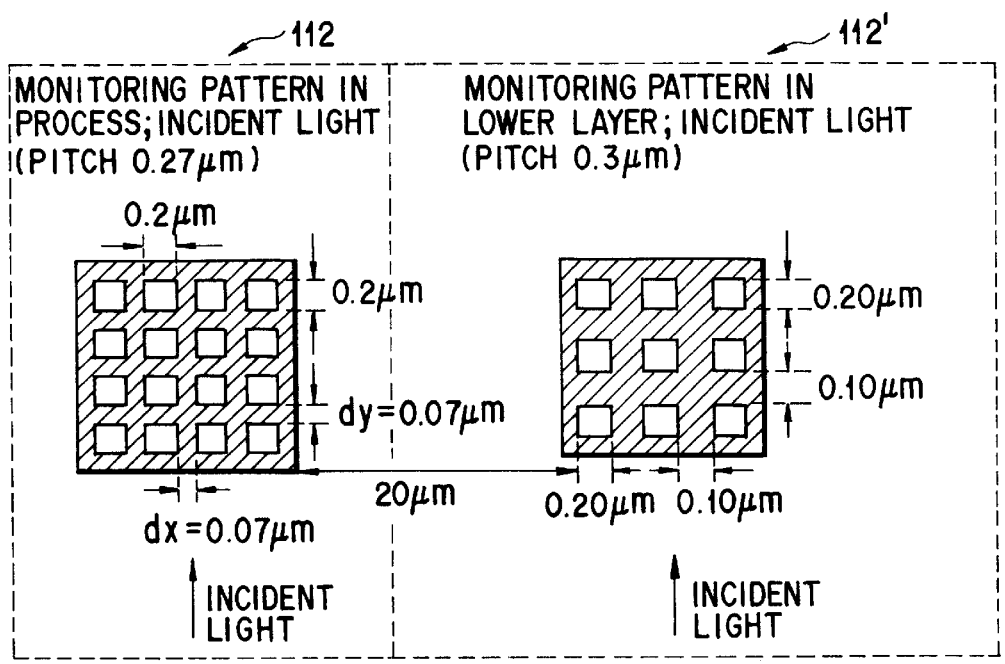
FIG. 9 is a view showing an example of a device pattern and an already processed pattern in a fourth embodiment.

FIG. 12 is a graph showing a relation between the developing time and the intensity of the diffracted light of order 0. A change in intensity of diffracted light of order 0 from a developing monitoring pattern 112 was larger than that of the device pattern 111 by a factor of 3 at a developing end time of a device pattern of 30 sec. An intensity of the diffracted light of order 0 from a pattern is a quantity which changes in proportion to an area left undeveloped and a larger change in intensity means a larger change in area.

The reason why a large change in the intensity in a monitoring pattern are that: (1) a change in shape of a hole pattern occurs more in a circumferential direction of a circle, (2) an area which is surrounded by three hole patterns is equal to or less than the limit of resolution, since holes are densely disposed, (3) a portion to be developed has a sectional shape which is narrower ahead and the like.

According to the present embodiment, where a developing monitoring pattern shown in FIG. 11 (L=0.2 μm, dx=dy= 0.06 μm) is employed and a CCD camera is used, a change of 1.5 nm (1%) in size of an L & S pattern of 0.15 nm can be monitored with 6 gradation units, so that more accurate control of a line width can be achieved, compared with the conventional technique which can monitor the pattern with 2 gradation units. Further, if a CCD camera with a 1024 gradation, further accurate control of a line width can be realized.

(The Sixth Embodiment)

Figure 13A:
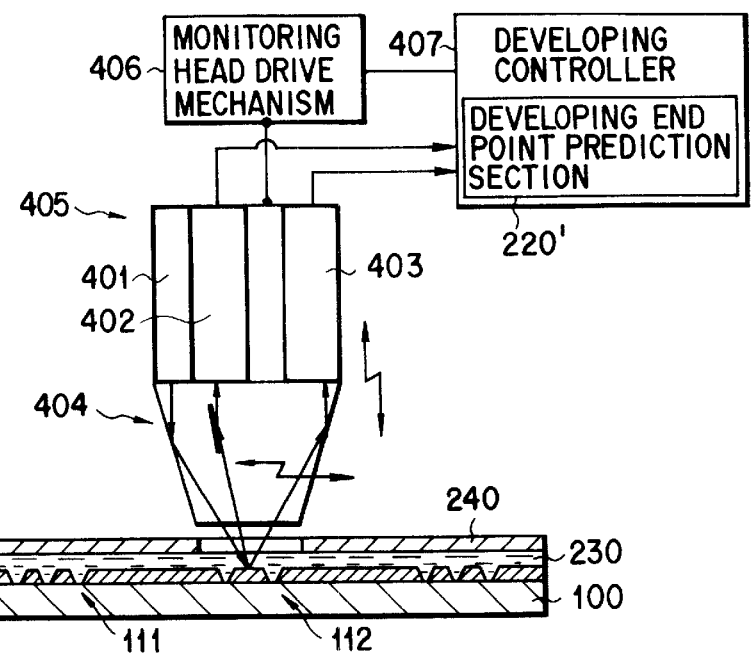
FIGS. 13A, 13B and 13C are views showing an example of a construction of an apparatus for performing pattern inspection during developing with use of diffracted light of order 0, which is a view for illustrating a six embodiment.

FIG. 13A is a schematic view showing the sixth embodiment of the present invention. The same constituent as that of the above mentioned embodiments (especially refer to the second embodiment) is attached by the same reference mark and descriptions on the same parts are omitted.

A part indicated-by 405 is a monitoring head. The monitoring head 405 comprises: a light source 401emitting parallel light rays shaped so as to have a wavelength of 330±5 nm by a narrow band filter; an order 1 diffracted light detector 402 recognizing diffracted light of order 1 from the monitoring pattern 112 as an image; and an order 0 diffracted light detector 403 recognizing diffracted light of order 0 from the device pattern 111 as an image.

The monitoring head 405 comprises a reflective optical system 404. The reflective optical system 404 has a function that the system guides projecting-in-or-out light from the wafer side 100 in a direction almost normal to the light source 401, order 1 diffracted light detector 402 and order 0 diffracted light detector 403.

In FIG. 13A, a developer 230 is present on a resist 110, a nozzle 240 in the shape of a disc is disposed and the monitoring head 405 is disposed in such a manner that a face for projecting-in-or-out light is opposed to the disc like nozzle 240.

Figure 13B:
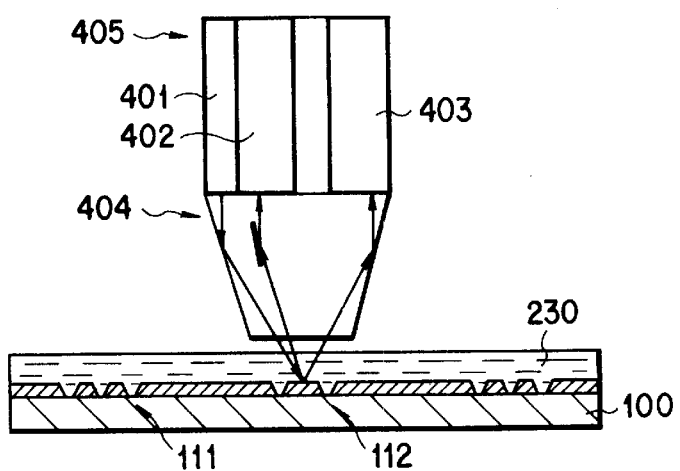
Figure 13C:
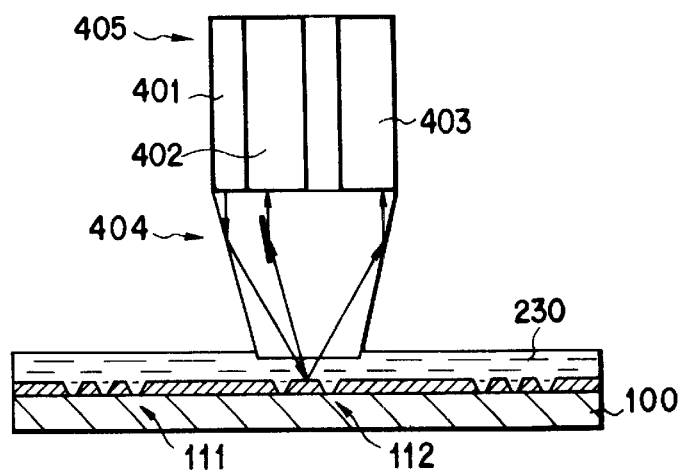

Views shown in FIGS. 13B and 13C are other examples of the monitoring head 405 in which they are otherwise disposed. That is, FIG. 13B shows an example in which the monitoring head 405 is disposed directly above the developer 230 and FIG. 13C is an example in which the monitoring head 405 is disposed in contact with the developer 230. Note that, the monitoring head 405 may be disposed in such a manner that a face for projecting-in-or-out light is located in the disc like nozzle 240, as is shown in FIG. 5.

The monitoring head 405 is held by a drive mechanism 406 which is used for driving in positioning of the monitoring head 405 in XYZ directions and the drive mechanism 406 is controlled by a developing controller indicated by 407 in FIG. 13A. The developing controller 407 is connected to the order 1 diffracted light detector 402 and order 0 diffracted light detector 403, the controller 407 detects positions of the monitoring pattern 112 and device pattern 111. The developing controller 407 comprises a developing end point prediction section 220' and the developing end point prediction section 220' is constituted so as to predict the developing end point based on an intensity of the 0 order diffracted light.

Figure 14A:
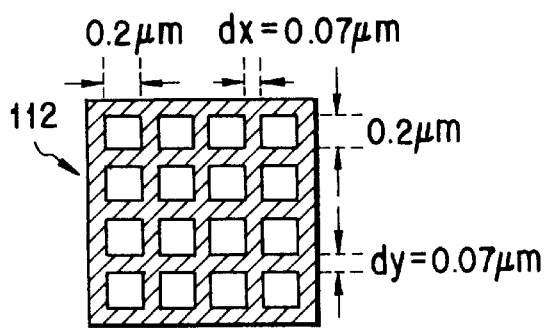
FIGS. 14A, 14B and 14C are views showing an example of monitoring pattern in the sixth embodiment.
Figure 14B:
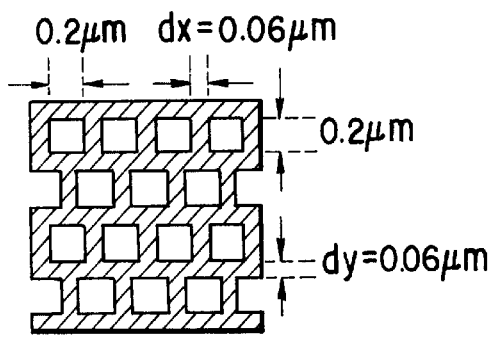
Figure 14C:
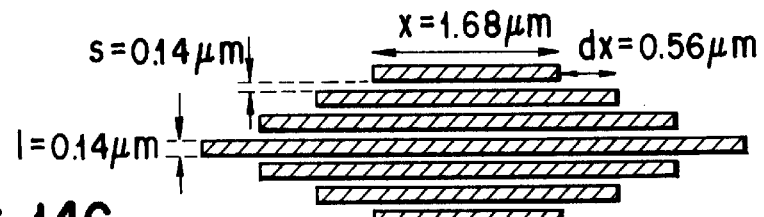

As the monitoring pattern 112, for example, patterns shown in FIGS. 14A to 14C are used. The pattern shown in FIG. 14A is the same as that shown and described in FIG. 2. The monitoring pattern 112 is disposed at a position-spaced from an area which contributes to formation of a device pattern within one shot.

In the present embodiment, an incident angle (angles hereinafter described are all to the monitoring pattern 112) of incident light on the monitoring pattern 112 is set 60 degrees, a detection angle of diffracted light of order 1 (107) from the monitoring pattern 112 is set 20 degrees and a detection angle of diffracted light of order 0 (108) is set 60 degrees.

An operation of the apparatus will be described.

Figure 15A:
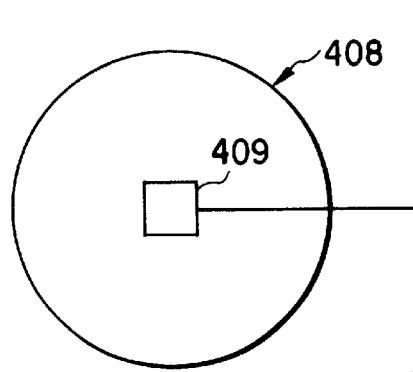
FIGS. 15A and 15B are views showing positioning of the monitoring head in the sixth embodiment.
Figure 15B:
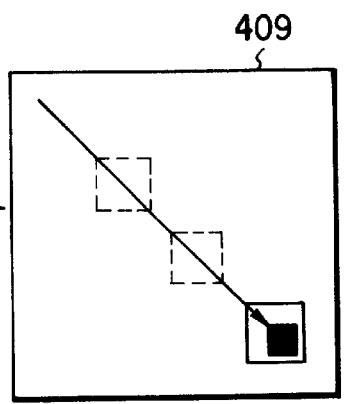

In FIG. 15A, 408 indicates a wafer and 409 indicates a chip on the wafer 408. After developing is started, the monitoring head 405 is moved to a monitoring pattern area in the chip 409 shown in FIG. 15B based on a shot map and data of a mask and detection of diffracted light of orders 1 and 0 is initiated. The monitoring head 405 enables observation of an area of 2×2 μmm at one time.

The monitoring pattern 112 has different pitches from a device pattern 111 and an already processed pattern. An incident angle of incident light is set at which only diffracted light of order 1 from the monitoring pattern 112 is detected by the order 1 diffracted light detector 402 of the monitoring head 405.

Therefore, since the order 1 diffracted light detector 402 does not detect light from a pattern (the device pattern 111 and already processed pattern) with a pitch other than 0.27 μm, only a portion of the monitoring pattern 112 is detected as a light spot on a detection screen of the order 1 diffracted light detector as shown in FIG. 16A.

On the other hand, the order 0 diffracted light detector 403 detects both of the device pattern 111 and the monitoring pattern 112 as images as shown in FIG. 16B. Since positional relations between pixels of images of the order 0 diffracted light detector 403 and the order 1 diffracted light detector 402 are already known, positional detection of the monitoring pattern 112 in a detection image of the order 0 diffracted light detector 402 can be performed as shown in FIG. 16C by a logical product between areas respectively detected by the order 1 diffracted light detector 402 and the 0 order diffracted light detector 403.

After such detection is performed, the controller 407 drives to move and rotate the monitoring head 405 so as to follow rotation of a wafer 100 during developing and further monitors an intensity of the order 0 diffracted light. The developing end point prediction section 220' refers to a relation obtained in advance between the size of an device pattern 111 and the intensity of the order 0 diffracted light of the monitoring pattern 112 and sets a time when the intensity of the diffracted light assumes a desired value as an end point in developing.

In such an embodiment, a monitoring head 405 of a one body type, which enables detection of diffracted light of orders 0 and 1 and scanning during developing, is used and a position of the monitoring pattern 112 is detected based on a detection position of diffracted light of order 1 from the monitoring patter 112.

Therefore, even when the device pattern 111 is disposed in a very narrow area or even when the device pattern 111 and the monitoring pattern 112 are similar in shape and in proximity to each other, positional detection of the monitoring pattern 112 can be achieved without a large change in an optical system.

In the controller 407 (the developing end point prediction section 220'), intensities of order 0 diffracted light and order 1 diffracted light may both be monitored. That is, a relation obtained in advanced between the size of the device pattern 111 and the intensities of orders 0 and 1 of diffracted light in the monitoring pattern 112 is referred and it is judged whether or not the device pattern 111 is finished to a desired size.

In such a manner, if the order 0 and 1 diffracted light is monitored at the same time, accuracy in measurement is further increased.

It is of course possible to apply the monitoring head 405 shown in the present embodiment to an apparatus for evaluation of a pattern size after developing.

(The Seventh Embodiment)

FIG. 17 is a schematic view showing the present embodiment. The same constituent as that of the sixth embodiment is indicated by the same mark and detailed descriptions on the same constituents are omitted.

A reflective optical system 502 provided in a monitoring head 501 of the present embodiment is constituted so that an incident angle of light emitted from a light source 401 to the monitoring pattern 112 (or the device pattern 111) is controlled so as to be an angle at which order 0 diffracted light returns to an order 0 diffracted light detector 403 almost in a direction normal thereto. That is, the order 0 diffracted light detector 403 is constituted so that it directly detects the order 0 diffracted light diffracted at the monitoring pattern 112.

In the reflective optical system 502, one pair of half mirrors 503, 504 is provided. One half mirror 503 is disposed on an incident light path and part of the incident light is branched to the other half mirror 504. The other half mirror 504 reflects the branched incident light and illuminates the monitoring pattern 112 in a condition that an optical path thereof coincides with an optical path of the diffracted light of order 0. The other half mirror 504 has the diffracted light of order 0 from the monitoring pattern 112 transmitted through itself and then guides the diffracted light to the order 0 diffracted light detector 403.

In this case, an incident angle of incident light to the monitoring pattern 112 is set 60 degrees and a detection angle of diffracted light of order 1 from the monitoring pattern 112 is set 20 degrees. A detection angle of diffracted light of order 0 is set 0 degree.

If such a constitution is adopted and a similar control to that of the sixth embodiment is performed, monitoring of diffracted light of order 0 from the monitoring pattern 112 can be achieved and thereby developing of the device pattern 111 can be monitored with good accuracy. According to the present embodiment, an effect can be obtained that an area to be developed of resist (the monitor pattern 112) can be monitored with better accuracy as described below.

That is, as shown in FIG. 18A, in the case of oblique incident light, since there is incident light 505 projected on the top of resist and incident light 506 projected between resist patterns, an area to be developed is not directly reflected on diffracted light of order 0.

However, in the present embodiment, as shown in FIG. 18B, since vertical incident light is adopted, an intensity of diffracted light of order 0 is expressed as the sum of diffracted light of order 0 (507) from the resist and diffracted light of order 0 (508) from an antireflection film. Thus, the area to be developed is directly reflected on the intensity. Therefore, since an intensity of light on which an area to be developed is reflected is obtainable, monitoring with better accuracy can be performed, compared with the sixth embodiment.

In the present embodiment, too, various kinds of apparatus configuration are considered, as shown in FIGS. 13B and 13C. Moreover, the monitoring head shown in the present embodiment may be applied to an apparatus with which pattern evaluation after developing is performed.

(The Eighth Embodiment)

FIG. 19 is a view showing a construction of an apparatus according to the eighth embodiment. The same constituent as that of the sixth and seventh embodiments is indicated by the same mark and description on the same constituent is omitted.

A monitoring head 601 of the present embodiment comprises an optical system indicated by 602 for detecting incident order 0 diffracted light in FIG. 19. The optical system 602 is constituted so that parallel light rays of a wave length of 260±5 nm shaped by a narrow band filter is projected in a monitoring pattern side and at the same time diffracted light of order 0 from the monitoring pattern 112 is detected as an image. Diffracted light of order 1 from the monitoring pattern 112 is detected by an order 1 diffracted light detector indicated by 603 shown in FIG. 19.

In the present embodiment, an incident angle to the monitoring pattern 112 of incident light is set 0 degree (angles shown hereinafter all are to the monitoring pattern), a detection angle of diffracted light of order 1 from the monitoring pattern 112 is set 74 degrees and a detection angle of diffracted light of order 0 is set 0 degree.

According to such a constitution, monitoring of developing can be performed by control similar to the sixth embodiment. Since an optical path of incident light to the monitoring pattern 112 coincides with an optical path of diffracted light of order 0, detection of diffracted light of order 0 on which an area to be developed is reflected can be performed.

In the present embodiment, too, various kinds of apparatus configuration are considered, as shown in FIGS. 13B and 13C. Needless to say that the constitution shown in the present embodiment can be applied to an apparatus with which pattern evaluation is conducted after developing.

(The Ninth Embodiment)

The ninth embodiment and the following embodiments are those in which a monitoring area different in shape from the first to eighth embodiments is used for monitoring. The same constituent as that of the first to eighth embodiments is indicated by the same mark and detailed description on the same constituent is omitted.

That is, while in the first to eighth embodiments the monitoring pattern 112 densely packed with holes is used as shown in FIG. 2, the monitoring area of the present embodiment does not have such pattern. FIG. 20 shows the monitoring area 701 according to the present embodiment. A developing speed of the monitoring area 701 is adjusted to a desired value only by setting an exposure dose.

In the present embodiment, an intensity of diffracted light of order 0 from the monitoring area 701 is monitored during developing of the device pattern 111 and developing is terminated when a film thickness of the monitoring area 701 reaches predetermined value, so that the device pattern 111 is finished to a desired size.

First of all, procedures of formation of the monitoring area 701 mill be described in a detailed manner.

In the present embodiment, exposure of a predetermined area of resist 110 coated on a wafer 100 is conducted using only by diffracted light of order 0 from an exposing mask to form the monitoring area 701. That is, exposure only by diffracted light of order 0 is conducted and thereby a pattern such as a hole or the like is prevented from being formed on the resist 110.

On exposure using an exposure mask, conditions that only diffracted light of order 0 from the exposure mask reaches the resist 110 are determined in the following manner using parameters of exposure wavelength $\lambda$, a converted pitch on a resist of a mask pattern p, NA and $\sigma$:

$$\lambda/p \geq (1 \pm \sigma)NA$$

Therefore, a pattern pitch on a mask pattern for the monitoring area 701 is determined by the formula. If an exposure mask having such a pitch is used, it can be prevented for a pattern to be formed on the resist since only diffracted light of order 0 of diffracted light transmitted through the exposure mask reaches the resist 110.

In the present embodiment, a transmittance of the exposure mask is properly adjusted to control an intensity of exposure against the resist 110 and a developing speed of the monitoring area 701 formed by the exposure is thereby adjusted so as to be a value suitable for monitoring. That is, a developing speed at which a small quantity of the resist in the monitoring area 701 is left behind at an end point in developing is calculated from a thickness of the resist 110 and a standard developing time for the resist 110 to the devise pattern 111.

An exposure dose (exposure dose to form the monitoring pattern 701) at which the developing speed is obtained is calculated from the obtained developing speed and a dissolution characteristic of the resist 110. A transmittance of the exposure mask for the monitoring area 701 against the exposure mask for the device pattern 111 is calculated from a ratio between an optimum exposure dose for formation of the device pattern 111 and the exposure dose for formation of the monitoring pattern 701.

Therefore, patterns for exposure are formed on the exposure mask for the monitoring area 701 with a pitch which satisfy the formula and on the exposure mask for the device pattern with a line width at which the transmittance can be obtained.

For example, in exposure conditions of an L & S pattern of 0.154 $\mu$m (NA: 0.6, an exposure wave length: 248 nm, $\sigma$: 0.75), a pitch of an exposure pattern with which only diffracted light of order 0 reaches to the resist 110 is 0.22 $\mu$m. In the case where an exposure dose is 7.2 $\mu$mJ at which a developing speed of the monitoring area 701 is 2 nm/sec (a film thickness changes to 30 nm in 60 sec developing), the transmittance is 36% if an optimum exposure dose of the device pattern 111 is 20 $\mu$mJ.

Therefore, in this case, if a line type pattern in which a pitch is 0.22 $\mu$m and a line width is designed so that a transmittance is 36% is adopted as a pattern for exposure for formation of the monitoring area 701, a desired monitoring area 701 can be formed.

A construction of an apparatus for monitoring developing with use of such a monitoring area 701 will be described in reference to FIG. 21.

In FIG. 21, a device pattern 111 is formed on resist 110 on a wafer (a substrate to be treated) 100 together with a monitoring area 701 in the present embodiment by means of a full-wafer exposure. The monitoring area 701 is disposed at a position separated from an area which contributes to formation of the device pattern within one shot.

Since the apparatus is a size monitoring apparatus which is applied during developing as that in the second embodiment, an developer 230 is present on the resist 110.

In the apparatus, parallel light rays which is almost monochromatic, having a narrowed band in the range of 410 nm with a half band width of 5 nm are projected to the monitoring area 701 from a light source 702. Diffracted light of order 0 from the monitoring area 701 is detected by an order 0 diffracted light detector (CCD camera) 703.

The light source 702 and the order 0 diffracted light detector 703 are connected to a controller 704 and operated based on an operation signal from the controller 704. That is, the controller 704 drives and positions the light source 702 and the order 0 diffracted light detector 703 at an opposed position to the monitoring area 701 based on detection of diffracted light of order 0 by the order 0 diffracted light detector 703. Monitoring using the order 0 diffracted light detector 704 is started in company with the start of developing.

Figure 22:
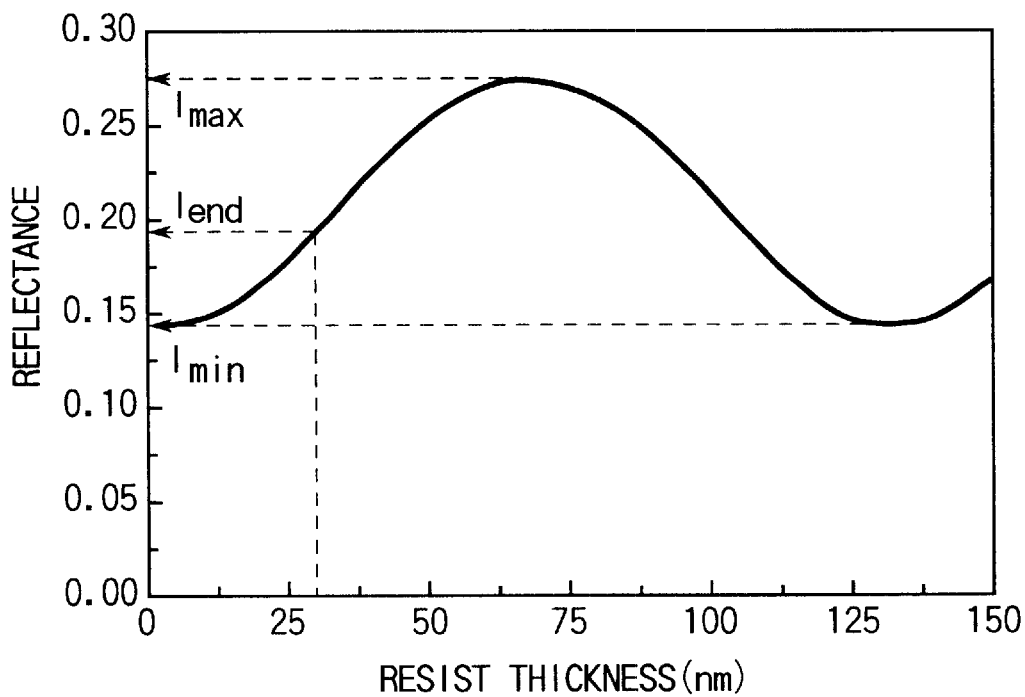
FIG. 22 is a graph showing a relation between the intensity of diffracted light of order 0 from the monitoring area shown in FIG. 20 and the resist thickness in the ninth embodiment.

The monitoring is performed by detecting an intensity of the diffracted light of order 0 from the monitoring area 701. That is, in the ideal case, a change in intensity of the diffracted light-of order 0 for a thickness of the monitoring area 701 is expressed with a curve having a maximum point $I'_{max}$ and a minimum point $I'_{min}$ as shown in FIG. 22. When an intensity of diffracted light of order 0 at a film thickness which is an end point in developing is indicated by $I'_{end}$, $I'_{end}$ is expressed in the following manner with use of a maximum point $I'_{max}$ and a minimum point $I'_{min}$.

$$I'_{end} = I'_{min} \pm (I'_{max} - I'_{min}) \times a$$

$$a = \frac{I'_{end} - I'_{min}}{I_{max} - I_{min}},$$

wherein (a) is a correction factor and obtained from intensities of diffracted light of order 0 at a maximum and a minimum $I'_{max}$, $I'_{min}$, and $I'_{end}$ which have been measured using preceding wafers and intensities of diffracted light of order 0 at a maximum and a minimum $I'_{max}$, $I'_{min}$ which are measured in the current developing. When the correction factor a is applied to the current measurements $I'_{max}$, $I'_{min}$, an intensity of diffracted light of order 0 at an end point in developing $I'_{end}$ can be obtained. The developing end point prediction section 220' terminates developing when an intensity of light detected by the order 0 diffracted light detector 703 assumes $I'_{end}$.

What is important in the present embodiment is a point that an end point in developing is predicted based of a maximum and a minimum of a change in intensity of diffracted light of order 0 as described above. Therefore, as a light for observation being oscillated from the light source 702, light of a wavelength with which a maximum and a minimum as described above can be obtained is required to be selectively used.

In the present embodiment, while it is described that there is no extremely large time difference between judgment of an end in developing and a reality thereof, if the time difference is not negligible, as an exposure intensity for the monitoring area 701, there may be set an intensity which is a remainder after an amount corresponding to the time difference is reduced.

According to such a constitution, since a developing time can be adjusted by monitoring a change in intensity of diffracted light of order 0 from the monitoring area 701, a similar effect to those of the first to eighth embodiments can be achieved.

Further, according to the present embodiment, the effects which will be described below can be achieved by using a monitoring area 701 which has no pattern.

That is, in the present embodiment, not only is diffracted light of order 0 from the monitoring area 701 which has no pattern monitored but also an end point in developing is predicted based on a maximum and a minimum of an intensity of light. When such a constitution is adopted, an end point in developing can correctly be predicted if a correction factor obtained not based on absolute values of a light intensity but based on known maximum and a known minimum is applied to the current measurements, even if an offset arises in an light intensity signal.

On the other hand, in the first to eighth embodiments, an absolute value of an intensity signal of diffracted light of order 0, is used for monitoring. In such a method, if an offset in a signal occurs for some cause of the other, there is a risk that an end point in developing cannot correctly be detected. Since an area to be developed of a pattern is reflected on an intensity signal in a constitution where incident light is projected from directly above a monitoring pattern and diffracted light of order 0 is detected, an intensity of diffracted light of order 0 changes in a linear fashion against a developing time as shown in FIG. 12. Therefore, in this case, too, monitoring is performed by using an absolute value of an intensity signal and thus there arises a chance where an end point in developing cannot correctly be detected.

However, according to the control of the present embodiment, such a fault is eliminated and as described above, there is an effect that an end point in developing can correctly be detected.

In this ninth embodiment, while a monitoring area 701 which comprises no pattern is used, a method in which a monitoring area is formed is not limited to those described in the present embodiment but other proper methods may be used for the formation. For example, in the present embodiment, while the monitoring area 701 has been fabricated by exposure to light with use of an exposure pattern of a predetermined pitch and a predetermined line width, a half tone film whose transmittance is properly set may be formed as an exposure mask.

(The Tenth Embodiment)

The present embodiment shows an example of the tenth embodiment.

FIG. 23 is schematic view showing the present embodiment.

In the present embodiment, the light source 702 comprises a lamp house 801 in which light can be subjected to dispersion in wavelength, an optical fiber 802 connected to the lamp house 801, and a collimating lens 803 mounted at the fore end of the optical fiber 802. The tip portion of the optical fiber 802 and the collimating lens 803 is held on a monitoring head 804 which is movable in XY directions.

Parallel light rays emitted from the lamp house 801 passes through the optical fiber 802 and the collimating lens 803 and then projected to the monitoring area 701. Diffracted light of order 0 from the monitoring area 701 passes through the optical fiber 806 connected to a lens 805 which is held by the monitoring head 804 and detected by the order 0 diffracted light detector 703 (CCD camera).

The monitoring head 804 is driven by a monitoring head drive device 807 of the monitoring head 807 is operated by instructions of the controller 704.

That is, the monitoring head 804 moves to a position of the monitoring area 701 and detects diffracted light of order 0 from the monitoring area 701. At this point, the monitoring head 804 moves to the monitoring area 701 based on a shot map of a wafer and a layout of a mask and thereafter an intensity of the monitoring area 701 is obtained while synchronizing with rotation of the wafer during developing.

Accuracy in inspection may be improved by adopting plural monitoring heads. As a monitoring head, it may be one having a shape shown in FIG. 13A and it is possible to adopt a proper shape other than that.

Note that, the monitor head of the present embodiment may be arranged in the same manner as shown in FIG. 5 or FIGS. 13A to 13C.

(The Eleventh Embodiment)

The present embodiment is an apparatus in which diffracted light of order 0 from a monitoring area 701 in developing is monitored as in the ninth and tenth embodiments and an end point of developing is judged. While, in the ninth embodiment, an end point in developing is judged based on an intensity of diffracted light of order 0, in the present embodiment, it is judged based on a developing time. Since the other points are similar to those of the ninth or tenth embodiments, descriptions thereon will be omitted.

Figure 24:
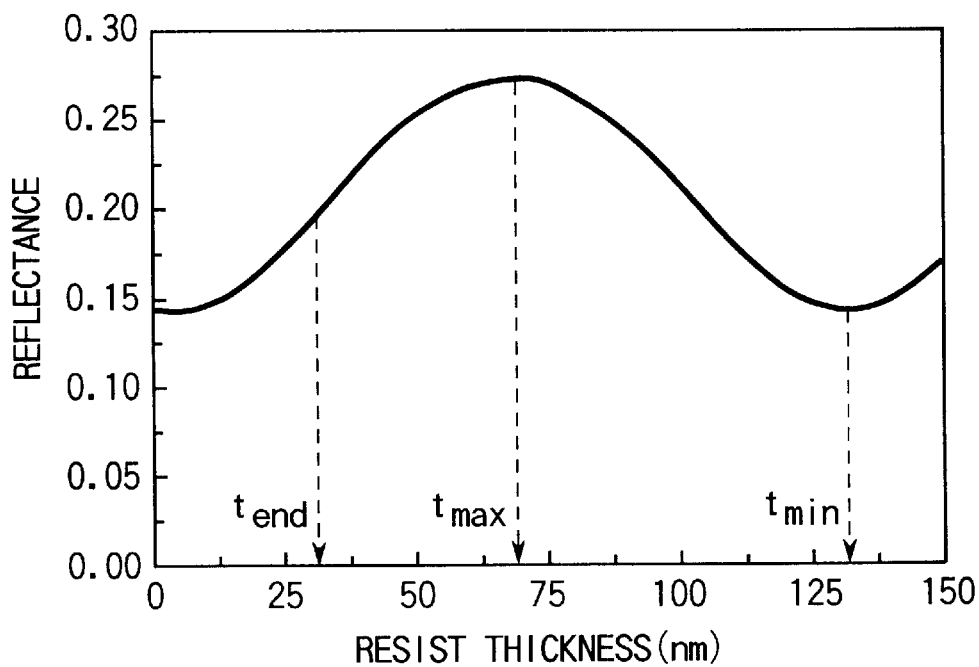
FIG. 24 is a graph showing a relation between the intensity of diffracted light from the monitoring area shown in FIG. 20 and the resist thickness, which is a graph for illustrating an eleventh embodiment.

FIG. 24 is a graph showing a relation between the film thickness of resist 110 and the intensity of diffracted light of order 0. In the present embodiment, a developing time $t'_{end}$ which is an end point in developing is predicted from a developing time at which an light intensity is a maximum or a minimum $t'_{max}$, $t'_{min}$ and developing is terminated at a developing time $t'_{end}$.

Figure 25:
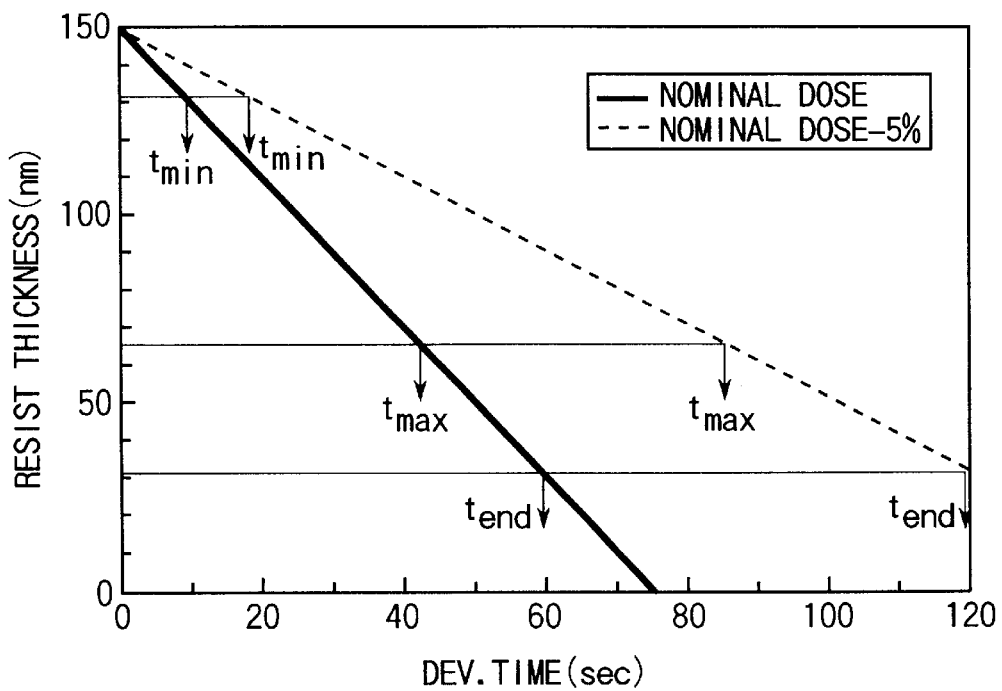
FIG. 25 is a graph showing a relation between the resist thickness and a development time, which is the graph for illustrating the eleventh embodiment.

If process conditions are respectively constant, a time when it is an end point in developing is constant. However, since there are a fluctuation in the conditions, a developing end time is not constant. If an exposure condition is fluctuated from a desired value by −5%, a decrease in thickness of a resist film for a developing time changes according to a dissolution characteristic of resist as shown in FIG. 25. At this point, times at which they are a minimum value, a maximum value and an end point in developing are respectively made indicated by $t'_{max}$, $t'_{min}$ and $t'_{end}$. In the present embodiment, a developing end time $t'_{end}$ which has been obtained in advance is multiplied by a correction factor a and thus a developing end time $t'_{end}$ in the current developing process is predicted.

$$t'_{end} = a \times t'_{end}$$

The correction factor (a) may be selected as a value with highest accuracy from values obtained from the following formula.

$$a = t'_{max}/t'_{max}$$

$$a = t'_{min}/t'_{min}$$

$$a = (t'_{max}/t'_{max} + t'_{min}/t'_{min})/2$$

A method in which a developing end time $t'_{end}$ is determined is not limited to this method but any proper method can be adopted as long as it is predicted based on times at which it is a maximum or a minimum, $t'_{min}$, $t'_{min}$, for example, a time which is when a predetermined interval is elapsed after $t'_{max}$ or the like.

(The Twelfth Embodiment)

While the present embodiment is to monitor diffracted light of order 0 as in the ninth and tenth embodiments, monitoring is performed by using two kinds of observation light having different wavelengths form each other.

That is, in the present embodiment, in a constitution shown in FIG. 23, light which has a narrowed band of a wavelength of 410 nm with a half band width of 5 nm and light which has a narrowed band of a wavelength of 600 nm with a half band width of 5 nm are alternately emitted from a lamp house 801.

Figure 26:
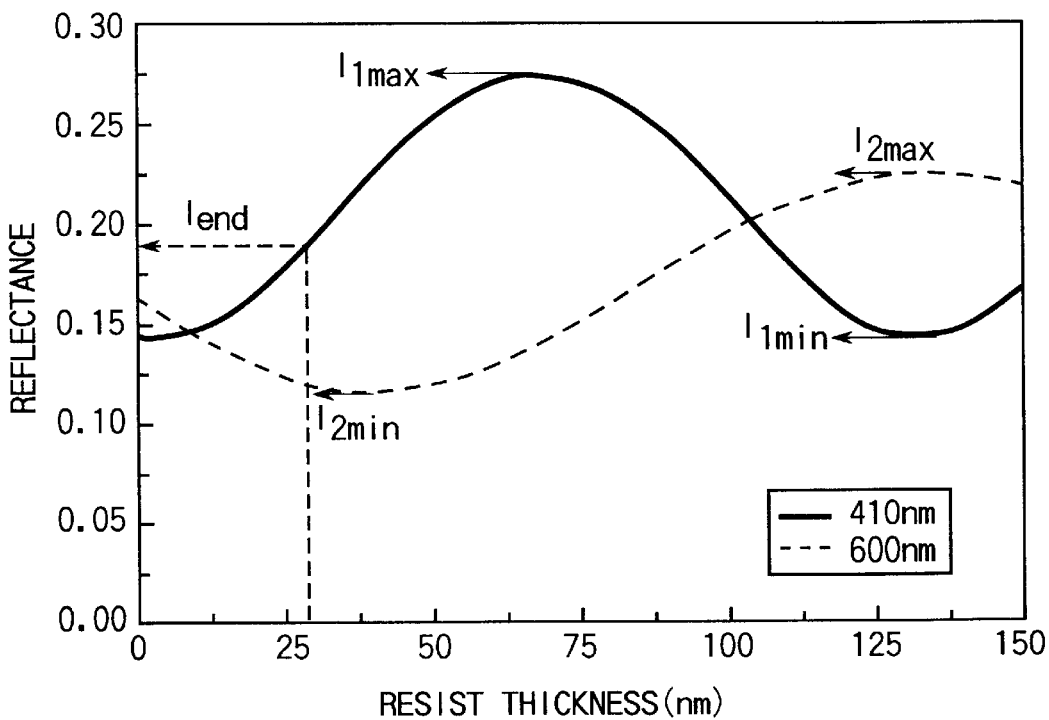
FIG. 26 is a graph showing a relation between the intensity of diffracted light of order 0 and the resist thickness when light of two different wavelengths is used for detection, which is a graph for illustrating a twelfth embodiment.

A controller 704 detects diffracted light of order 0 from both kinds of light alternately by a CCD camera 703. In an ideal case, the changes in intensity of diffracted light from both kinds of the light vs. the resist film thickness are shown in FIG. 26.

Intensities of diffracted light of order 0 at a maximum, a minimum and an end point in developing in the case of a wavelength of 410 nm are respectively indicated by $I_{1max}$, $I_{1min}$, $I^{1end}$ and intensities at a maximum and a minimum in the case of a wavelength of 600 nm are respectively indicated by $I_{2max}$, $I_{2min}$. On the other hand, in the current developing, intensities of diffracted light of order 0 at a maximum, a minimum in the case of a wavelength of 410 nm are respectively indicated by $I_{1'max}$, $I_{1'min}$ and intensities at a maximum and a minimum in the case of a wavelength of 600 nm are respectively indicated by $I_{2'max}$, $I_{2'min}$. An intensity at an end point in developing $I_{1'end}$ can be obtained by use of a correction factor a and the following formula:

$$I_{1'end} = I_{1'min} + (I_{1end} - I_{1min}) \times a$$

$$a = \frac{I_{1'max} - I_{1'min}}{I_{1max} - I_{1min}} + \frac{I_{2'max} - I_{2'min}}{I_{2max} - I_{2min}} \times 1/2$$

According to such a constitution, light of different wavelengths are used and correction is performed using both detection values of the light of different wavelengths, so that diffracted light of order 0 at an end point in developing can be predicted with better accuracy.

A method in which correction accuracy is improved by use of different wavelengths as in the present embodiment can be applied to a method in which a time $t'_{end}$ at which developing is terminated is predicted from times when an intensity is a maximum or a minimum, $t'_{max}$, $t'_{min}$.

Figure 27:
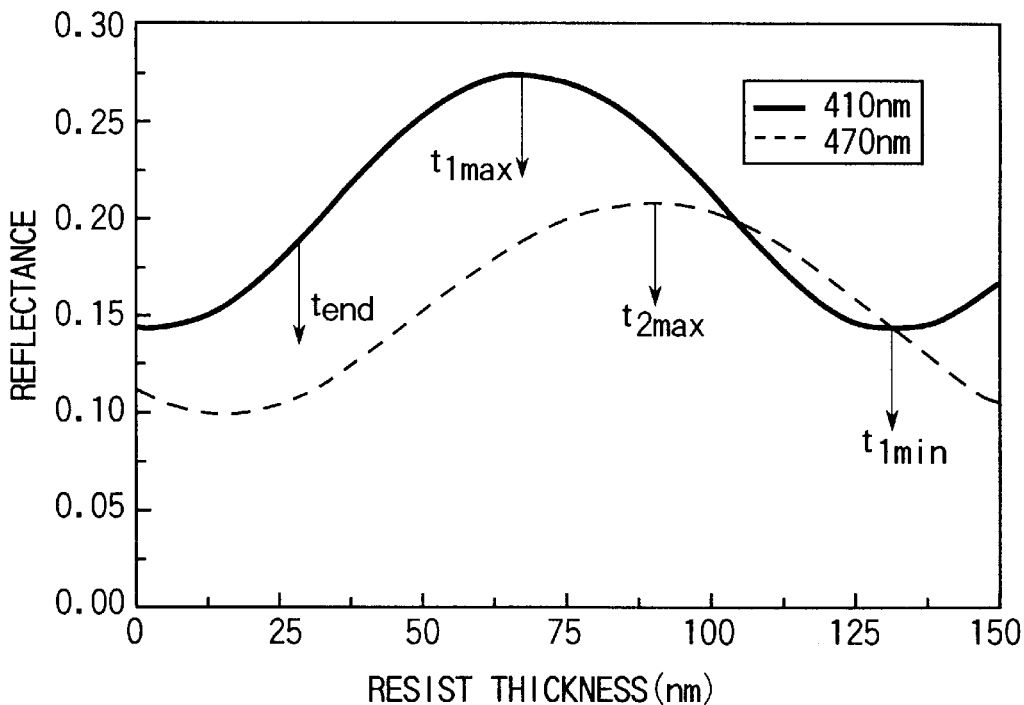
FIG. 27 is a graph showing a relation between the intensity of diffracted light of order 0 and the resist thickness when light of two wavelengths is used for detection, which is a graph for illustrating another measurement example of the twelfth embodiment.

That is, in an ideal case, the changes in intensity of diffracted light of order 0 of wavelengths of 410 nm and 470 nm against the film thickness of a resist film are shown in FIG. 27.

Figure 28:
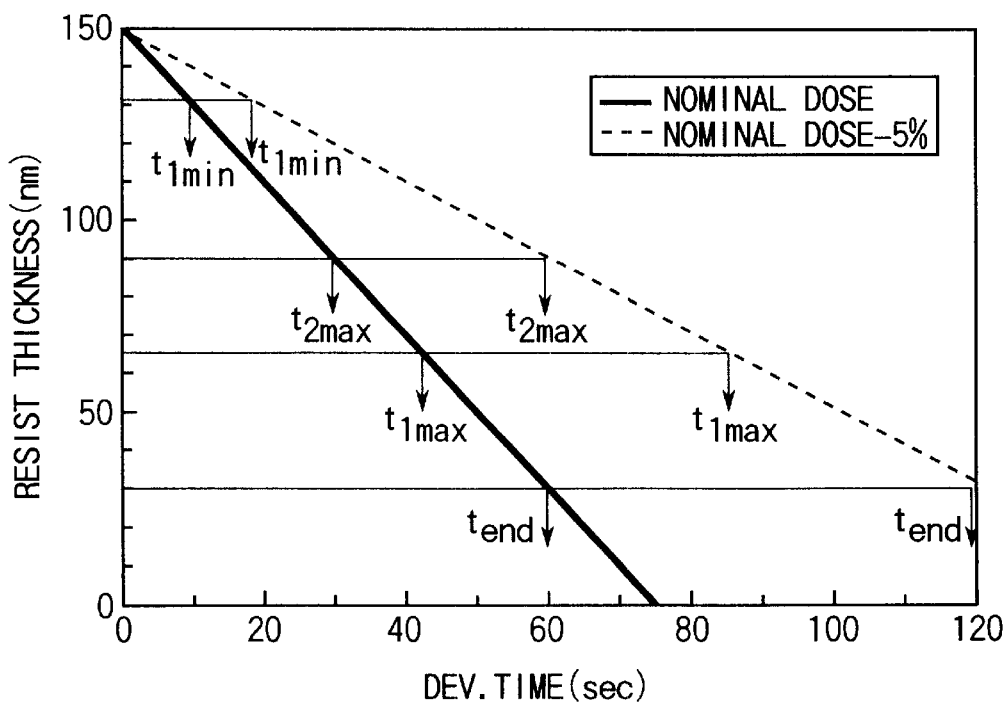
FIG. 28 is a graph showing a relation between the resist thickness and the development time when light of two wavelengths is used for detection, which is a graph for illustrating still another measurement example of the twelfth embodiment.
Figure 29:
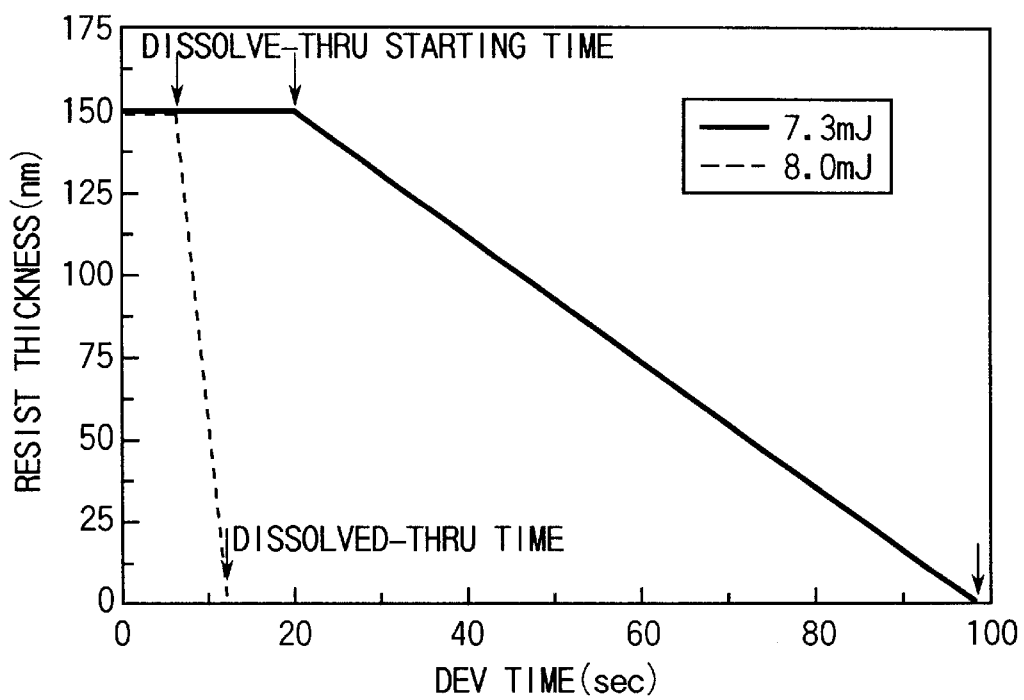
FIG. 29 is a graph showing a relation between the resist thickness and the development time, which is a view for illustrating a thirteenth embodiment.

At this point, times when intensities of diffracted light of order 0 from light of a wavelength of 410 nm are respectively indicated by $t_{1max}$, $t_{1min}$, $t_{1end}$. A time at which an intensity of diffracted light of order 0 is a maximum is indicated by $t_{2max}$. when process conditions are respectively constant; a developing time may be constant, but there is a fluctuation in actual process conditions. If a condition for an exposure dose is fluctuated by −5% of a desired value, the decrease in film thickness vs. the developing time is shown in dependence on a dissolution characteristic of a resist in FIG. 28.

In this case, times at which intensities of diffracted light of order 0 from light of a wavelength of 410 nm are respectively a maximum, a minimum and an end point of developing are indicated by $t_{1'max}$, $t_{1'min}$, $t_{1'end}$ and a time at which diffracted light of order 0 from light of a wavelength of 470 nm is a maximum is indicated by $t_{2'max}$. Among the times, $t_{1max}$, $t_{1min}$, $t_{1end}$, $t_{2max}$ are obtained in advance and if diffracted light of order 0 is detected during developing, $t_{1'max}$, $t_{1'min}$, $t_{2'max}$ can be obtained. A time of an end point in developing $t'_{end}$ can be obtained from these values by the following formula:

$$t'_{end} = a \times t_{end}$$

$$a = (t_{1'max}/t_{1max} + t_{1'min}/t_{1min} + t_{2'max}/t_{2max})/3$$

Therefore, if developing is terminated at trend in a similar manner to in the eleventh embodiment, an end point in developing can correctly be controlled.

(The Thirteenth Embodiment)

The present embodiment is to monitor diffracted light of order 0 from a monitoring area 701 in a similar manner to in the ninth embodiment, but as resist 110, there is adopted resist which has a dissolution characteristic that a film thickness is not decreased for the initial duration of developing but is started to be decreased after some seconds pass.

The monitoring area 701 is designed so that decrease in film thickness is started at an end point of developing of the device pattern 111. That is, in the case where a resist is employed whose exposure dose at which decrease in film thickness is started after 60 sec of developing passes is 6.6 mJ, transmittance of an exposure mask for a monitoring area is designed to be 22%, since an optimum exposure dose for the device pattern 111 is 30 mJ (6.6/30=22%).

Figure 31:
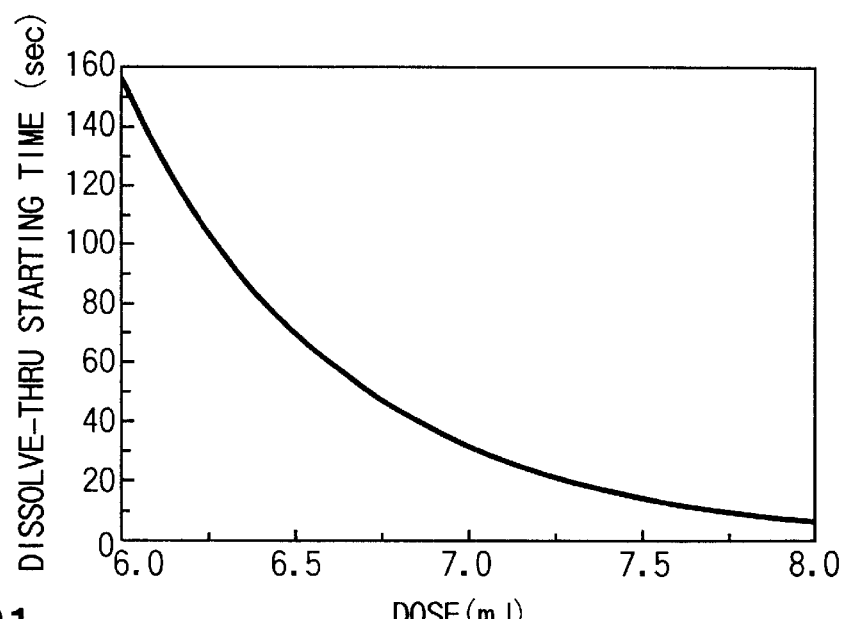
FIG. 31 is a graph showing a relation between the exposure time and the resist dissolve-thru starting time, which is a view for illustrating the thirteenth embodiment.

A relation between the dissolve-thru starting time and the exposure dose for a monitoring area 701 is shown in FIG. 31.

In the case where process conditions are constant, a developing time may be 60 sec all the time, but if a proper exposure dose for the device pattern 111 changes from 30 mJ to 29 mJ, sufficient developing cannot be achieved in 60 sec. However, in the present embodiment, since the dissolve-thru time starting time of the monitoring area 701 is detected, such a change in process conditions can be responded and thereby end point control is correctly conducted all the time.

That is, if an exposure time for the device pattern 111 changes from 30 mJ, which is a proper value, to 29 mJ, a new exposure dose of the monitoring area 701 is 6.4 mJ since an exposure dose of the monitoring area 701 is 22% of the value. Therefore, in this case, dissolve-thru is started after 80 sec passes. Thus, if dissolve-thru is detected and it is regarded as an end point in developing, a change in process conditions can be responded.

Detection of dissolve-thru starting or ending can be detected based on a change in intensity of diffracted light of order 0.

Note that, the present embodiment can use dissolve-thru ending time(shown in FIG. 30) to determine end point in developing.

In this case, the monitoring area 701 is designed so that a film thickness is almost zero at an end point of developing of the device pattern 111. That is, in the case where a resist is employed whose exposure dose at which decrease in film thickness is started after 60 sec of developing passes is 7.5 mJ, transmittance of an exposure mask for a monitoring area is designed to be 25%, since an optimum exposure dose for the device pattern 111 is 30 mJ (7.5/30=25%).

Figure 30:
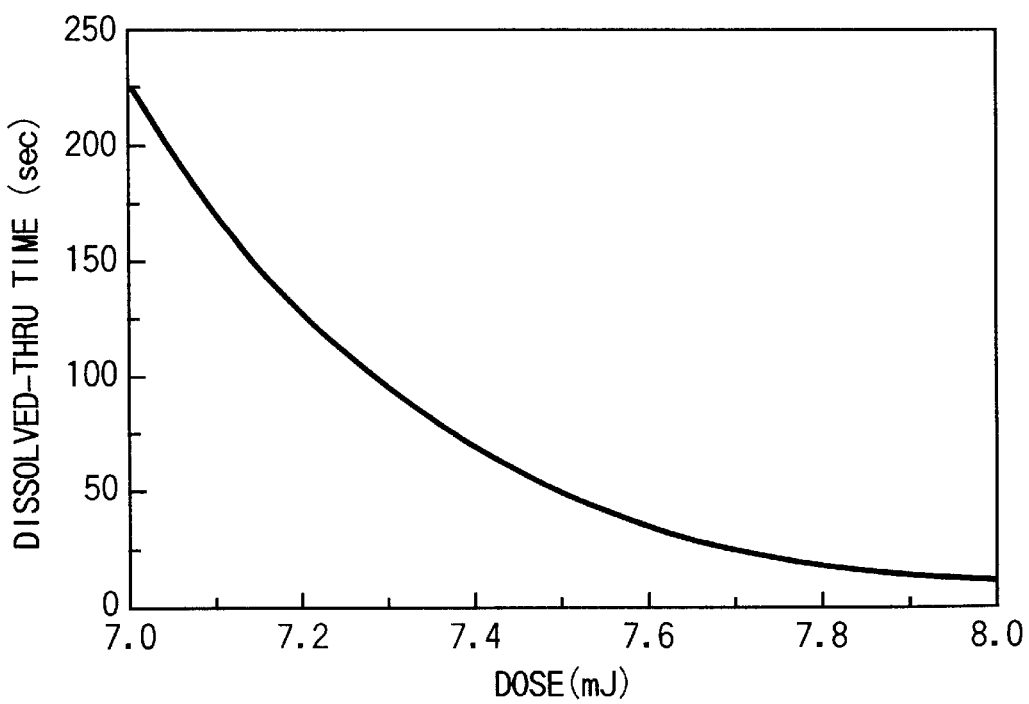
FIG. 30 is a graph showing a relation between the exposure time and the resist dissolved-thru time, which is a view for illustrating the thirteenth embodiment.

A relation between the dissolved-thru ending time and the exposure dose for a monitoring area 701 is shown in FIG. 30.

In the case also, where process conditions are constant, a developing time may be 60 sec all the time, but if a proper exposure dose for the device pattern 111 changes from 30 mJ to 29 mJ, sufficient developing cannot be achieved in 60 sec. However, in the present embodiment, since the dissolve-thru ending time of the monitoring area 701 is detected, such a change in process conditions can be responded and thereby end point control is correctly conducted all the time.

That is, if an exposure time for the device pattern 111 changes from 30 mJ, which is a proper value, to 29 mJ, a new exposure dose of the monitoring area 701 is 7.25 mJ since an exposure dose of the monitoring area 701 is 25% of the value. Therefore, in this case, dissolve-thru is started after 110 sec passes. Thus, if dissolve-thru ending is detected and it is regarded as an end point in developing, a change in process conditions can be responded.

Detection of dissolve-thru starting or ending can be detected based on a change in intensity of diffracted light of order 0.

(The Fourteenth Embodiment)

Figure 32:
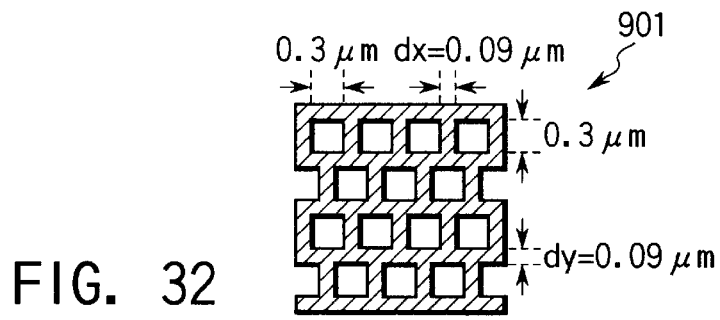
FIG. 32 is a view showing an example of a monitoring pattern used in a fourteenth embodiment.

The present embodiment employs a pattern monitoring apparatus having a similar constitution to that in the ninth embodiment and is concerned with an apparatus monitoring a monitoring pattern 901 in which centers of holes are respectively located at vertexes of a regular hexagon in FIG. 32.

The monitoring pattern 901 is disposed in an area of $10 \times 10$ $\mu m^2$ which is separately positioned from an area which contributes to formation of a device within one shot.

Figure 33:
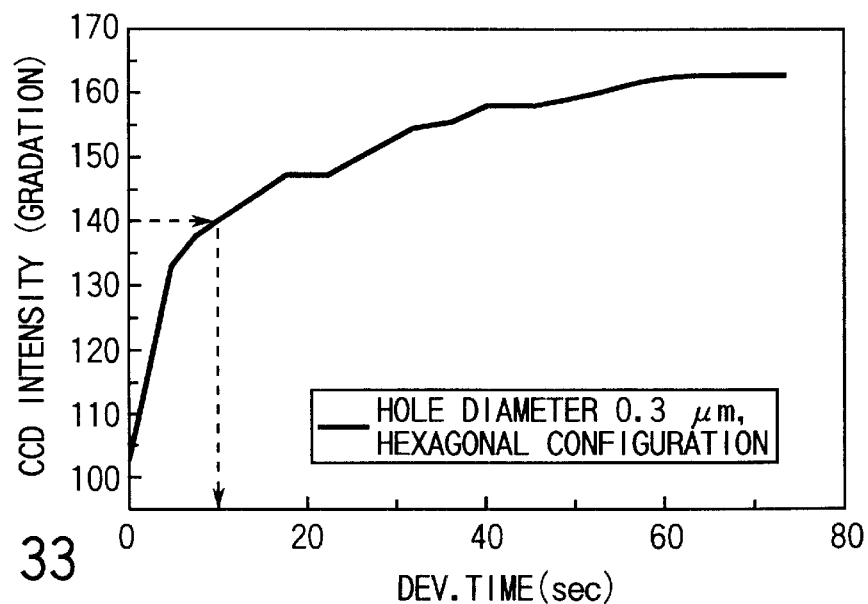
FIG. 33 is a graph showing a relation between the intensity of diffracted light of order 0 and the development time, which is a view for illustrating the fourteenth embodiment.

A relation between the developing time and the intensity of diffracted light of order 0 is shown in FIG. 33. In the case of the monitoring pattern 901 of the present embodiment, direct detection of an end point in developing is hard since a change in intensity at the end point in developing (after 60 sec) is not so large. For this reason, in the present embodiment, a part which shows a large change in intensity in the initial duration of developing is detected by an order 0 diffracted light detector and an end point in developing is predicted based on the detected value. As a prediction method, for example, a threshold value is set as 140 and a time after 50 sec passes the threshold value is regarded an end point in developing.

Since the present embodiment has such a constitution, in the case where the monitoring pattern showing a small change in intensity at the end point in developing is monitored, too, an effect is achieved that an end point in developing can correctly be detected in a comparative sense.

The present invention is not restricted to the first to fourteenth embodiments. For example, a shape of an element pattern, a pitch of repetition, the number of repetition and the like can properly be changed according to a specification. A monitoring pattern may be formed in an empty area in a useful part of a chip in adjacent manner to a device pattern and it may be formed on a dicing line.

Illumination light on a monitoring pattern is not limited to light which is employed in the embodiments but any light may be used as far as a wavelength does not optically activate resist and it is a single wavelength (or light having a narrow band). In pattern inspection after developing, it is not required for light to be of a wavelength which is inactive to the resist. Means for detecting diffracted light from a monitoring pattern is not limited to a CCD camera but any device which can detects a change of intensity may be used.

In the present embodiment, detection of diffracted light of order 1 in a vertical direction in oblique incidence illumination and detection of diffracted light of order 0 in a vertical direction in vertical illumination are conducted, detection of diffracted light of order 0 in an oblique direction in oblique incidence illumination and detection of diffracted light of order 1 in an oblique direction in vertical illumination may be used. An exposure is not limited to light but x rays or an electron beam can be used instead.

Needless to say that various changes in or modifications of the embodiments can be made in execution of the present invent as far as they fall within the scope of the present invention.

As described above, according to the present invention, a monitoring pattern which is different from a device pattern or an already processed pattern, especially diffracted light from which has a large change in intensity thereof over an elapsed time of developing is used for pattern evaluation and thereby a resist pattern can be inspected in a short time with high accuracy and furthermore, accurate size control of a resist pattern can be performed on a different wafer by controlling a developing time based on the inspection.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A pattern size evaluation method for evaluating a size of a device pattern which is formed by exposing a resist film on a to-be-processed substrate, developing the device pattern, and evaluating the size of the device pattern based on a monitoring pattern formed at the same time as the device pattern on the to-be-processed substrate, comprising the steps of:

designing the monitoring pattern, the monitoring pattern being arranged to form a resist monitoring pattern composed of juxtaposed pattern elements having a pitch that is less than a pitch of elements of the device pattern, the monitoring pattern also being arranged such that a rate of change of intensity of reflected light from the monitoring pattern is greater than a rate of change of intensity of reflected light from the device pattern at an end of a developing step;

exposing the resist film by a mask including both the device pattern and the designed monitoring pattern within one shot;

developing the exposed resist film to form the device pattern and the monitoring pattern of the resist;

illuminating the monitoring pattern with a parallel light of a predetermined wavelength after the developing step;

detecting the intensity of diffracted light obtained from the monitoring pattern; and evaluating the size of the device pattern based on the intensity of the diffracted light from and only from the monitoring pattern having been exposed to only substantially the same amount of radiation as the device pattern.

2. A pattern size evaluation method according to claim 1, wherein the monitoring pattern is made to have a pitch different from that of the device pattern so that the diffracted light from the monitoring pattern can be detected separately from diffracted light from the device pattern.

3. A pattern size evaluation method according to claim 1, wherein a direction in which the pattern elements of the monitoring pattern are periodically arranged is made to have a direction different from that of the device pattern so that the diffracted light from the monitoring pattern can be detected separately from the diffracted light from the device pattern.

4. A pattern size evaluation method according to claim 1, wherein the size evaluation of the device pattern is performed based on an intensity of a diffracted light of order 0 or a diffracted light of order 1 from the monitoring pattern.

5. A pattern size evaluation method for evaluating a size of a device pattern which is formed by exposing a resist film on a to-be-processed substrate, developing the device pattern and evaluating the size of the device pattern based on a monitoring pattern formed in the same time as the device pattern on the to-be-processed substrate, comprising the steps of:

designing a monitoring pattern area which causes decrease in film thickness gradually in a uniform manner in company with progress of the developing;

exposing the resist film by a mask that includes both the device pattern and the monitoring pattern within one shot;

developing the exposed resist film to form the device pattern and the monitoring pattern of the resist;

illuminating the monitoring pattern with a parallel light of a predetermined wavelength after the developing step;

detecting the intensity of diffracted light obtained from the monitoring pattern area; and evaluating the size of the device pattern based on the intensity of the diffracted light from and only from the monitoring pattern area having been exposed to only substantially the same amount of radiation as the device pattern.

6. A pattern size evaluation method according to claim 5, wherein the mask used to form said monitoring pattern has a regular pattern within a pattern pitch $p$ satisfying a condition defined by an equation:

$$\lambda/p \geq (1+\sigma)NA$$

where $\lambda$ is an exposure wavelength, $\sigma$ is a coherence factor, and NA is a numerical aperture at which only 0 order diffracted light can reach at a substrate being processed in the condition of the exposing step, and an area ratio of light transmitting apertures and light shielding portions of the mask are designed to have a light transmission factor of less than 90%.

7. A pattern size evaluation method according to claim 5, wherein the size evaluation of the device pattern is performed based on an intensity of a diffracted light of order 0 obtained from the monitoring pattern area.

8. A pattern forming method for forming a device pattern by exposing a resist film on a to-be-processed substrate, developing the exposed device pattern, and forming the device pattern, comprising the steps of:

designing a monitoring pattern, the monitoring pattern being arranged to form a resist monitoring pattern composed of juxtaposed pattern elements having a pitch that is less than a pitch of elements of the device pattern, the monitoring pattern also being arranged such that a rate of change of intensity of reflected light from the monitoring pattern is greater than a rate of change of intensity of reflected light from the device pattern at an end of a developing step;

exposing the resist film by a mask including both the device pattern and the monitoring pattern within one shot;

developing the resist film exposed using the mask;

illuminating the monitoring pattern being formed during the developing step with a parallel light of a predetermined wavelength;

detecting the intensity of diffracted light obtained from the monitoring pattern being developed;

evaluating the size of the device pattern based on the intensity of the diffracted light from and only from the monitoring pattern having been exposed to only substantially the same amount of radiation as the device pattern; and controlling the developing time of the device pattern based on a result of the size evaluation of the device pattern.

9. A pattern forming method according to claim 8, wherein the parallel light illuminated on the monitoring pattern has at least two wavelengths.

10. A pattern forming method for forming a device pattern by exposing a resist film on a to-be-processed substrate, developing the exposed device pattern, and forming the device pattern, comprising the steps of:

designing a monitoring pattern which causes decrease in film thickness gradually in a uniform manner in company with progress of the developing;

exposing the resist film by a mask that includes both the device pattern and the monitoring pattern within one shot;

developing the resist film exposed by the mask;

illuminating the monitoring pattern being formed during the developing step with a parallel light of a predetermined wavelength;

detecting the intensity of diffracted light obtained from the monitoring pattern being developed;

evaluating the size of the device pattern based on the intensity of the diffracted light from and only from the monitoring pattern having been exposed to only substantially the same amount of radiation as the device pattern; and controlling developing time of the device pattern based on a result of the size evaluation.

11. A pattern size evaluation method according to claim 10, wherein the mask used to form said monitoring pattern has a regular pattern with a pattern pitch p satisfying a condition defined by an equation $$\lambda/p \geq (l+\sigma)NA$$

where $\lambda$ is an exposure wavelength, $\sigma$ is a coherence factor, and NA is a numerical aperture at which only 0 order diffracted light can reach at a substrate being processed in the condition of the exposing step, and an area ratio of light transmitting apertures and light shielding portions of the mask are designed to have a light transmission factor of less than 90%.

12. A pattern forming method according to claim 10 wherein the parallel light illuminated on the monitoring pattern has at least two wavelengths.

13. A pattern forming method according to claim 10 wherein the light illuminating the monitoring pattern has a wavelength at which the intensity of diffracted light varying with the reduction in the film thickness of the monitoring pattern has maximum and minimum values; and the evaluation of the device pattern size is performed based on the maximum and minimum values of the intensity of the diffracted light variation to detect a developing stopping time.

* * * * *

UNITED STATES PATENT AND TRADEMARK OFFICE
CERTIFICATE OF CORRECTION

PATENT NO. : 6,423,977 B1
DATED : July 23, 2002
INVENTOR(S) : Hayasaki et al.

It is certified that error appears in the above-identified patent and that said Letters Patent is hereby corrected as shown below:

Column 22,
Line 21, "$\lambda/p \geq (1+\sigma)NA$" should read -- $\lambda/\rho \geq (1+\sigma)NA$ --.
Line 23, "a is a coherence" should read -- $\sigma$ is a coherence --.

Column 24,
Line 1, "pitch p" should read -- pitch $\rho$ --.
Line 4, "$\lambda/p \geq (1+\sigma)NA$" should read -- $\lambda/\rho \geq (1+\sigma)NA$ --.

Signed and Sealed this

Eighteenth Day of March, 2003

JAMES E. ROGAN
*Director of the United States Patent and Trademark Office*